(12) United States Patent
Rodan et al.

(10) Patent No.: US 12,139,555 B2
(45) Date of Patent: Nov. 12, 2024

(54) PEPTIDES AND COMPOSITIONS FOR INHIBITING HAIR GROWTH

(71) Applicant: RODAN & FIELDS, LLC, San Francisco, CA (US)

(72) Inventors: Kathryn P. Rodan, Oakland, CA (US); Kathy A. Fields, San Francisco, CA (US); John Simon Craw, San Francisco, CA (US)

(73) Assignee: RODAN & FIELDS, LLC, San Francisco, CA (US)

( * ) Notice: Subject to any disclaimer, the term of this patent is extended or adjusted under 35 U.S.C. 154(b) by 0 days.

(21) Appl. No.: 17/779,307

(22) PCT Filed: Dec. 3, 2020

(86) PCT No.: PCT/US2020/062996
§ 371 (c)(1),
(2) Date: May 24, 2022

(87) PCT Pub. No.: WO2021/113434
PCT Pub. Date: Jun. 10, 2021

(65) Prior Publication Data
US 2023/0002447 A1 Jan. 5, 2023

Related U.S. Application Data

(60) Provisional application No. 62/942,862, filed on Dec. 3, 2019.

(51) Int. Cl.
*C07K 7/06* (2006.01)
*A61K 8/64* (2006.01)
*A61Q 7/02* (2006.01)
*C07K 5/093* (2006.01)
*C07K 5/103* (2006.01)
*C07K 5/11* (2006.01)
*C07K 5/113* (2006.01)

(52) U.S. Cl.
CPC ............ *C07K 7/06* (2013.01); *A61K 8/64* (2013.01); *A61Q 7/02* (2013.01); *C07K 5/0819* (2013.01); *C07K 5/101* (2013.01); *C07K 5/1019* (2013.01); *C07K 5/1021* (2013.01)

(58) Field of Classification Search
CPC .......... C07K 7/06; C07K 8/64; C07K 5/0819; C07K 5/101; C07K 5/1019; C07K 5/1021; A61Q 7/02; A61K 8/64
See application file for complete search history.

(56) References Cited

U.S. PATENT DOCUMENTS

| | | | |
|---|---|---|---|
| 5,856,456 A | 1/1999 | Whitlow et al. | |
| 6,025,325 A * | 2/2000 | Campfield | C07K 14/5759 424/193.1 |
| 7,304,129 B2 * | 12/2007 | Saffell | C07K 5/1021 435/375 |
| 10,010,613 B2 | 7/2018 | Castillo et al. | |
| 2008/0234183 A1 | 9/2008 | Hallbrink et al. | |
| 2011/0206704 A1 * | 8/2011 | Ganesan | G01N 33/573 435/7.1 |
| 2012/0251455 A1 | 10/2012 | Imamura et al. | |
| 2016/0117441 A1 * | 4/2016 | Bremel | G16B 20/30 706/21 |
| 2016/0137698 A1 | 5/2016 | Skerra et al. | |
| 2017/0135950 A1 | 5/2017 | Najafi | |

OTHER PUBLICATIONS

SEQ ID No. 12010 from Bremel US 20160117441, published on Apr. 28, 2016. (Year: 2016).*
Kubala J, "What's the Difference Between Synthetic and Natural Nutrients?," Nutrition, May 26, 2021, pp. 1-12. (Year: 2021).*
Anderson et al., "A Peptide from the First Fibronectin Domain of NCAM Acts as an Inverse Agonist and Stimulates FGF Receptor Activation, Neurite Outgrowth and Survival," J. Neurochem. 95(2):570-583 (2005).
Blanpain et al., "Self-Renewal, Multipotency, and the Existence of Two Cell Populations within an Epithelial Stem Cell Niche," Cell 118 (5):635-648 (2004).
Enevoldsen et al., "Neuroprotective and Memory Enhancing Properties of a Dual Agonist of the FGF Receptor and NCAM," Neurobiology of Disease 48(3):533-545 (2012).
Havlickova, "A Human Folliculoid Microsphere Assay for Exploring Epithelial-Mesenchymal Interactions in the Human Hair Follicle," Journal of Invest. Dermatol. 129(4):972-983 (2009).
Higgins et al., "Microenvironmental Reprogramming by Three-Dimensional Culture Enables Dermal Papilla Cells to Induce De Novo Human Hair-Follicle Growth," Proc. Natl. Acad Sci. USA 110(49):19679-19688 (2013).
International Search Report and Written Opinion for International PCT Application No. PCT/US2020/062996 (Apr. 23, 2021).
Kawano et al., "Comprehensive Analysis of FGF and FGFR Expression in Skin: FGF18 is Highly Expressed in Hair Follicles and Capable of Inducing Anagen from Telogen Stage Hair Follicles," J. Invest. Dermatol. 124(5):877-885 (2005).
Kimura-Ueki et al., "Hair Cycle Resting Phase is Regulated by Cyclic Epithelial FGF18 Signaling," J. Invest. Dermatol. 132(5):1338-1345 (2012).

(Continued)

*Primary Examiner* — Julie Ha
(74) *Attorney, Agent, or Firm* — Goodwin Procter LLP

(57) ABSTRACT

Synthetic peptides which have been shown to be FGF18 agonists are described. Topical compositions for decreasing, eliminating, or suppressing hair growth are disclosed herein. Methods for reducing hair growth, improving the appearance of skin, kits, and related cosmetic formulations are also provided herein.

20 Claims, 4 Drawing Sheets
Specification includes a Sequence Listing.

(56) References Cited

OTHER PUBLICATIONS

Li et al., "Neuritogenic and Neuroprotective Properties of Peptide Agonists of the Fibroblast Growth Factor Receptor," Int. J. Mol. Sci. 11(6):2291-2305 (2010).

* cited by examiner

PEPTIDES AND COMPOSITIONS FOR INHIBITING HAIR GROWTH

CROSS-REFERENCE TO RELATED APPLICATIONS

This application is a national stage application of PCT/US2020/062996 filed Dec. 3, 2020, which claims priority to U.S. Provisional Application No. 62/942,862 filed Dec. 3, 2019, which are incorporated herein by reference in their entirety.

SUMMARY

Embodiments disclosed herein are directed to fibroblast growth factor 18 (FGF18) agonist peptide comprising up to six amino acids in length selected from the group consisting of SEQ ID NO:1, SEQ ID NO: 2, SEQ ID NO:3, SEQ ID NO:4, SEQ ID NO:5, SEQ ID NO: 6, SEQ ID NO: 7, SEQ ID NO: 8, SEQ ID NO:9, SEQ ID NO:10, SEQ ID NO:11, SEQ ID NO:12, and PEPTIDE NO:15.

Embodiments disclosed herein are directed to topical compositions comprising one or more FGF18 agonist peptides as described herein, and a cosmetically acceptable excipient.

Embodiments are directed to methods for decreasing, diminishing, or suppressing hair growth in a subject comprising topically administering to the target location on the subject the FGF18 agonist peptide as described herein.

Embodiments are directed to methods for eliminating or suppressing hair growth in a subject comprising topically administering to the target location on the subject the FGF18 agonist peptide as described herein.

Embodiments are directed to methods for improving skin appearance in a subject comprising topically administering to the target location on the subject the FGF18 agonist peptide as described herein.

DETAILED DESCRIPTION

Figure 1:
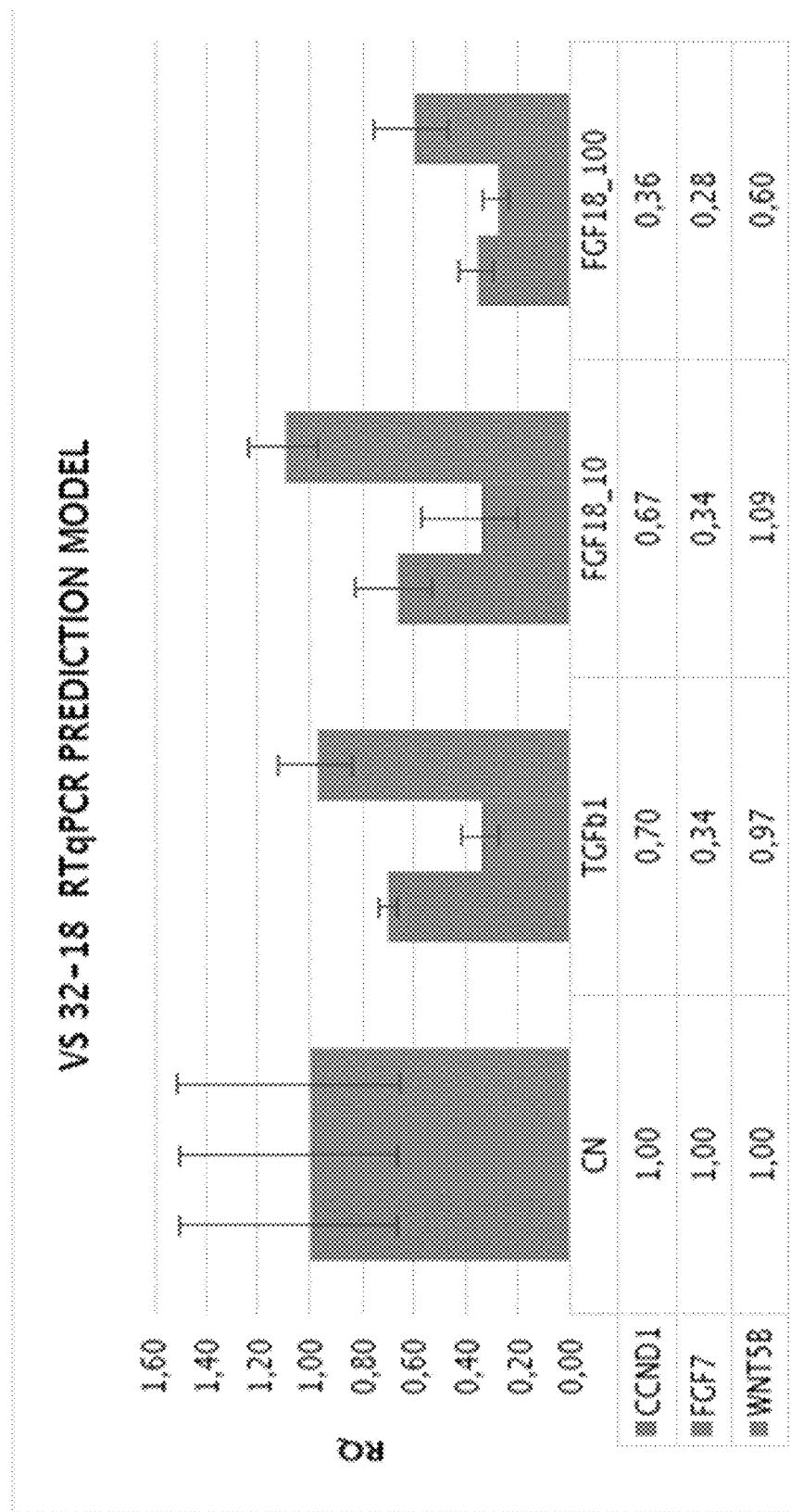
FIG. 1 is a graph showing the expression level of selected genes reported for a pool of 20 µHF presented as RQ (relative quantification) value and Error (max and min).

Hair follicle (HF) is a peculiar skin organ of mammals, which is developed from the bottom of primitive epidermis into the more internal dermal skin layer. The plug of cells known as follicle or dermal papilla exists in the base of the hair follicle and papilla is essential in normal circulation of the hair follicle and in growth of the hair shaft. The hair shaft is a collection of thread-shaped epithelial cells that are composed of keratin filaments and filament-aggregating proteins tightly attached thereto.

Human hair follows a growth cycle with three distinct phases: anagen, catagen, and telogen phases. The hair growth cycle is regulated by hormones or many growth factors. Severe stress or malnutrition may advance the catagen and telogen phases, leading to severe hair loss (alopecia). In male pattern baldness, the hair follicles at the front and top of the scalp are sensitive to androgen, which causes the follicles to miniaturize, thereby resulting in hair loss.

Likewise, in the converse, there are many situations where it would be desirable to inhibit hair growth in a safe, easy, and effective manner. Therefore, the development of effective and safe active agents are needed in this field.

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only, and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein is not entitled to antedate such disclosure by virtue of prior invention.

It must also be noted that as used herein and in the appended claims, the singular forms "a," "an," and "the" include plural reference unless the context clearly dictates otherwise.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with FGF18 agonist peptide or composition comprising one or more FGF agonist peptides, can include, but is not limited to, providing one or more FGF18 agonist peptides into or onto the target tissue. "Administering" a composition may be accomplished by topical administration, or by another suitable technique.

As used herein "agonist" is understood to be a substance that initiates a physiological response when combined with a receptor; and specifically an FGF18 agonist peptide is one that functions to interact with the FGF18 receptor and can induce a regressive hair follicle catagen phase, which produces a decrease in hair growth. Additionally, the peptide FGF18 agonist can induce or prolong a quiescent hair follicle state (telogen), which also produces a decrease in hair growth.

The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, which do not materially change the basic or novel properties of the specified FGF18 agonist peptide, the method of its use. As a nonlimiting example, an FGF18 peptide agonist which consists essentially of a recited amino acid sequence may also include one or more amino acids that do not materially affect the properties of the FGF18 peptide agonist.

The term "consists of" excludes any element, step, or ingredient not specified in the embodiment or claim.

In embodiments or claims where the term comprising is used as the transition phrase, such embodiments and claims can also be envisioned with replacement of the term "comprising" with the terms "consisting of" or "consisting essentially of" The compositions and methods of the present disclosure can comprise, consist essentially of, or consist of, the components disclosed.

FGF18 as used herein is understood to be fibroblast growth factor 18 (FGF18, also known as: FGF-18, and ZFGF5). The human coding sequence is described in Gene ID 8817, and GenBank Accession No.: NM_003862.2 (and further as part of GenBank Accession No: NC_000005.10). The human protein sequence is described at GenBank Accession No.: NP_003853.1.

Various alignments described herein refer to FGF receptors and growth factors. Below are GenBank references for their sequences.

FGF1(fibroblast growth factor 1): coding sequence can be found at Gene ID: 2246, which also includes links for the "RefSeqs" for the different isoforms (mRNA sequences, protein sequences).

FGFR1 (fibroblast growth factor receptor 1): coding sequence can be found at Gene ID: 2260, which also which also includes links for the "RefSeqs" for the different isoforms (mRNA sequences, protein sequences).

FGFR3 (fibroblast growth factor receptor 3): coding sequence can be found at Gene ID: 2261, which also which also includes links for the "RefSeqs" for the different isoforms (mRNA sequences, protein sequences).

FGFR2 (fibroblast growth factor receptor 2): coding sequence can be found at Gene ID: 2263, which also which also includes links for the "RefSeqs" for the different isoforms (mRNA sequences, protein sequences).

FGF2 (fibroblast growth factor 2): coding sequence can be found at Gene ID: 2247, which also which also includes links for the "RefSeqs" for the different isoforms (mRNA sequences, protein sequences).

As used herein "hair" means hair on the scalp, head, face, or body, including but not limited to hair on the scalp, hair of the eyelashes, hair of the eyebrows, mustache, beard, pubic hair, or hair on body parts including but not limited to upper lip, chin, underarms, groin, pubic, arms, legs, back, or neck.

The term "improve" is used to convey that the compounds of embodiments herein change either the appearance, form, characteristics and/or the physical attributes of the tissue to which it is being provided, applied or administered.

As used herein, to administer two or more agents "in combination" means that the individual agents are administered concurrently or within a time interval such that the physiological effects of the agents on the subject overlap. The two or more agents may or may not be administered in the same formulation or preparation.

As used herein "inhibiting or suppressing or reducing hair growth" means decreasing the growth rate of the hair, including, but not limited to, the reduction of the growth of hair and making it less visible to the eye, resulting in a smoother skin surface. In certain embodiments, the FGF18 agonist peptide induces a regressive hair follicle catagen phase, which produces a decrease in hair growth (e.g. functioning to inhibit or reduce hair growth). In certain embodiments, the peptide induces or prolongs a quiescent hair follicle state (telogen), which produces a decrease in hair growth. In certain embodiments, the FGF18 agonist peptide both induces the catagen phase and induces or prolongs the telogen hair follicle state.

By "pharmaceutically acceptable", it is meant the carrier, diluent or excipient must be compatible with the other ingredients of the topical composition and not deleterious to the recipient thereof "Cosmetically acceptable" has an analogous meaning.

The terms "polypeptide," "peptide" and "protein" are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, N-terminal capping with such agents as acetates, palmitates or other acceptable molecules that may or may not improve stability or skin penetration, and ADP-ribosylation.

Unless otherwise indicated, the term "skin" means that outer integument or covering of the body, consisting of the dermis and the epidermis and resting upon subcutaneous tissue. It is understood to be the layers which comprise it, from the uppermost layer or stratum corneum to the lowermost layer or hypodermis, both inclusive. These layers are composed of different types of cells such as keratinocytes, fibroblasts, melanocytes, mast cells, neurons and/or adipocytes among others. The term "skin" also includes the scalp. For the avoidance of doubt, the term "skin" does not include mucosal surfaces or nails.

The term "subject" as used herein includes, but is not limited to, humans and non-human vertebrates such as wild, domestic, and farm animals. In certain embodiments, the subject described herein is an animal. In certain embodiments, the subject is a mammal. In certain embodiments, the subject is a human. In certain embodiments, the subject is a non-human animal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

As used herein, the term "therapeutic" means an agent utilized to treat, combat, inhibit, ameliorate, prevent or improve an unwanted condition or disease of a patient.

A "therapeutically effective amount" or "effective amount" is an amount that achieves the desired effect, e.g. inhibiting, decreasing, diminishing, suppressing, or preventing hair growth. The specific amount administered/applied according to this invention to obtain the desired effects will, of course, be determined by the particular circumstances surrounding the case, including, for example, the compound administered, the route of administration, concomitant therapies and the local condition of the skin and/or hair. However, it will be understood that the effective amount administered will be determined by the practitioner or physician in the light of the relevant circumstances including the condition to be treated, the choice of compound to be administered, and the chosen route of administration, and therefore the above dosage ranges are not intended to limit the scope of embodiments herein in any way. A therapeutically effective amount of an FGF18 agonist peptide or composition comprising the FGF18 agonist peptide is typically an amount such that when it is administered in a physiologically tolerable excipient composition, it is sufficient to achieve an effective local concentration in the tissue target and is used interchangeably with a "cosmetically effective amount" of an FGF18 agonist peptide or composition comprising the FGF18 agonist peptide.

The term "treatment", as used herein, refers to the administration of an FGF18 agonist peptide or composition comprising the FGF18 agonist peptide according to the invention to alleviate or eliminate an undesired condition, in this case to diminish, decrease, lessen, or prevent hair growth. The terms "treat," "treated," or "treating" as used herein refers to both treatment and prophylactic or preventative measures, wherein the object is to inhibit, prevent or slow down (lessen) an undesired physiological condition, e.g. hair growth, or to otherwise obtain beneficial or desired results (e.g. to inhibit, lessen, decrease, delay, retard, slow down or prevent hair growth). As used herein, "treatment" may be considered a cosmetic effect and not a therapeutic effect.

The phrase "target location," as used herein, refers to the place on the body the individual will apply the topical composition. The "target location" can be where hair naturally grows, such as the skin of the scalp, face, legs, arms, or pubic area. The "target location" can also be where hair is abnormally growing.

FGF18 Agonist Peptides

In embodiments described herein, the FGF18 agonist peptides encompass any peptide comprising up to six amino acids in length selected from the group consisting of SEQ ID NO:1, SEQ ID NO: 2, SEQ ID NO:3, SEQ ID NO:4, SEQ ID NO:5, SEQ ID NO: 6, SEQ ID NO: 7, SEQ ID NO: 8, SEQ ID NO:9, SEQ ID NO:10, SEQ ID NO:11, SEQ ID NO:12, and PEPTIDE NO:15.

These FGF18 agonist peptides are listed in Table 1. The FGF18 agonist peptides exhibiting particularly desirable activity include SEQ ID NO: 2, SEQ ID NO: 6, SEQ ID NO: 7, and SEQ ID NO: 8.

TABLE 1

FGF18 agonist peptides

| SEQUENCE | Reference Label | Activity |
|---|---|---|
| KQLR (SEQ ID NO: 1) | P1 | +/- |
| RTGQYK (SEQ ID NO: 2) | P2 | * |
| DRLK (SEQ ID NO: 3) | P3 | U |
| EKTD (SEQ ID NO: 4) | P4 | +/- |
| EKDD (SEQ ID NO: 5) | P5 | +/- |
| KRTG (SEQ ID NO: 6) | P6 | ** |
| EKND (SEQ ID NO: 7) | P7 | ** |
| DRDE (SEQ ID NO: 8) | P8 | * |
| DKSE (SEQ ID NO: 9) | P9 | U |
| DRVE (SEQ ID NO: 10) | P10 | U |
| DRTD (SEQ ID NO: 11) | P11 | U |
| IEKV (SEQ ID NO: 12) | P12 | U |
| DRV (PEPTIDE NO: 15) | P13 | +/- |

** = best activity
* = good activity
+/- = some activity
U = no activity detected The SEQ ID NO:'s and PEPTIDE NO correspond to the P numbers, which are used in data and graphs as described in the Examples.

As used herein, the term "FGF18 agonist peptide" refers to a peptide that exhibits the desired biological activity, which includes exhibiting fibroblast growth factor 18 (FGF18) agonist activity, and further induces a regressive hair follicle catagen phase, or preventing the hair follicle from entering the anagen phase, resulting in a decrease or suppression in hair growth; and also induces or prolongs a quiescent hair follicle state (telogen), resulting in a decrease in hair growth. "FGF18 agonist peptide" refers to a peptide that binds FGF18. Thus, FGF18 agonist peptide is used in the broadest sense and specifically covers, but is not limited to, FGF18 agonist peptides as described and listed in Table 1.

In other embodiments the invention provides FGF18 agonist peptides that specifically bind FGF18 and that have at least 50%, 60%, 70%, 75%, 80%, 85%, 90%, 95%, 98% or 99% sequence identity with any of SEQ ID NOs: 1-12 and PEPTIDE NO: 15 (as shown in Table 1), while still exhibiting the desired binding and biological activities. Typically, an FGF18 agonist peptide retains at least 10% of its FGF18 binding activity. Preferably, an FGF18 agonist peptide retains at least 20%, 30%, 40%, 50%, 60%, 70%, 80%, 90%, 95% or 100% or more of the FGF18 binding affinity compared with the FGF18 agonist peptides of Table 1. It is also intended that an FGF18 agonist peptide can include conservative amino acid substitutions that do not substantially alter its biologic activity. In additional embodiments, the invention provides FGF18 agonist peptides having up to 0, 1, 2, 3, 4, or 5 amino acid substitutions, while still exhibiting the ability to bind to FGF18 and exhibit the desired biological activity (e.g. functional property) described herein.

A "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Various embodiments of the FGF18 agonist peptides of the present invention comprise polypeptides with the sequences disclosed herein, e.g. SEQ ID NOs: 1, 2, 3, 4, 5, 6, 7, 8, 9, 10, 11, 12, and PEPTIDE: 15 (as shown in Table 1), or polypeptide chains comprising up to 1, 2, 3, 4, or 5 conservative amino acid substitutions. Exemplary conservative substitutions are set forth in Table 2.

TABLE 2

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Sequence identity refers to the degree to which the amino acids of two polypeptides are the same at equivalent positions when the two sequences are optimally aligned. Sequence similarity includes identical residues and non-identical, biochemically related amino acids. The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M.O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M.O. Dayhoff (ed.), pp. 353-358, Natl. Biomed. Res. Found., Washington, D.C.; Altschul, S.F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S.F. "Evaluating the statistical significance of multiple distinct local alignments." in Theoretical and Computational Methods in Genome Research (S. Suhai, ed.), (1997) pp. 1-14, Plenum, N.Y.

In certain embodiments, the FGF18 agonist peptide is SEQ ID NO:2, SEQ ID NO:6, SEQ ID NO:7, or SEQ ID NO:8.

In certain embodiments, the FGF18 agonist peptide is SEQ ID NO:1, SEQ ID NO:4, SEQ ID NO:5, or PEPTIDE NO: 15.

In certain embodiments, the FGF18 agonist peptide is SEQ ID NO:3, SEQ ID NO:9, SEQ ID NO:10, SEQ ID NO:11, or SEQ ID NO:12.

In certain embodiments, the FGF18 agonist peptide comprising the amino acid sequence KQLR (SEQ ID NO:1). In certain embodiments, the FGF18 agonist peptide comprising the amino acid sequence RTGQYK (SEQ ID NO: 2). In certain embodiments, the FGF18 agonist peptide comprising the amino acid sequence DRLK (SEQ ID NO:3). In certain embodiments, the FGF18 agonist peptide comprising the amino acid sequence EKTD (SEQ ID NO:4). In certain embodiments, the FGF18 agonist peptide comprising the amino acid sequence EKDD (SEQ ID NO:5). In certain embodiments, the FGF18 agonist peptide comprising the amino acid sequence KRTG (SEQ ID NO: 6). In certain embodiments, the FGF18 agonist peptide comprising the amino acid sequence EKND (SEQ ID NO: 7). In certain embodiments, the FGF18 agonist peptide comprising the amino acid sequence DRDE (SEQ ID NO: 8). In certain embodiments, the FGF18 agonist peptide comprising the amino acid sequence DKSE (SEQ ID NO:9). In certain embodiments, the FGF18 agonist peptide comprising the amino acid sequence DRVE (SEQ ID NO:10). In certain embodiments, the FGF18 agonist peptide comprising the amino acid sequence DRTD (SEQ ID NO:11). In certain embodiments, the FGF18 agonist peptide comprising the amino acid sequence IEKV (SEQ ID NO:12). In certain embodiments, the FGF18 agonist peptide comprising the amino acid sequence DRV (PEPTIDE NO:15).

In additional embodiments, the FGF18 agonist peptide has at its N-terminal a protection group selected from the group consisting of acetyl group, fluorenyl methoxy carbonyl group, formyl group, palmitoyl group, myristyl group, stearyl group, linoleate group, polyethylene glycol (PEG), or other cosmetically acceptable protecting groups. In additional embodiments, the FGF18 agonist peptide has at its C-terminal a protection group selected from the group consisting of acetyl group, fluorenyl methoxy carbonyl group, formyl group, palmitoyl group, myristyl group, stearyl group, linoleate group, polyethylene glycol (PEG), or other cosmetically acceptable protecting groups.

In some embodiments, 2 or more of the same or different FGF18 agonist peptides described herein are covalently linked to each other either directly or via a linker. In some embodiments, the linker comprises poly-glycine, poly-proline, poly-alanine, glycine and serine, or alanine and proline. Exemplary linker include $(GS)_n$, wherein n is 2-10; $(G_nS)$, wherein n is 2-10; or $(AP)_n$, wherein n is 2-20. The FGF18 agonist peptides may be linked to each other in an N- to C-direction. The use of naturally occurring as well as artificial peptide linkers to connect polypeptides into novel linked fusion polypeptides is well known in the literature (Hallewell et al., J Biol Chem 264, 5260-5268, 1989; Alfthan et al., Protein Eng. 8, 725-731, 1995; Robinson & Sauer, Biochemistry 35, 109-116, 1996; U.S. Pat. No. 5,856, 456). In certain embodiments, 2 or more of the FGF18 agonist peptides described herein are linked using a linking moiety which can be any moiety recognized by those skilled in the art as suitable for joining short peptides so long as the peptides retain the ability to interact with FGF18. The linking moiety may be comprised of, for example, but not limited to, a disulfide bond, a carbonyl moiety, a hydrocarbon moiety optionally substituted at one or more available carbon atoms with a lower alkyl substituent.

In certain embodiments, the FGF18 agonist peptide binds to fibroblast growth factor 18 (FGF18), resulting in a decrease or suppression of hair growth. In certain embodiments, the FGF18 agonist peptide induces a regressive hair follicle catagen phase, or preventing the transition to anagen, resulting in a decrease in hair growth.

In certain embodiments, the FGF18 agonist peptide induces or prolongs a quiescent hair follicle state (telogen), resulting in a decrease or suppression in hair growth.

In embodiments, the amino acids of the FGF18 agonist peptides can be in either D or L form. In embodiments, the amino acids of the FGF18 agonist peptides are in L form.

In addition, in some embodiments, the FGF18 agonist peptides of the invention are acylated at the N-terminal amino acid of the peptide. In other embodiments, the FGF18 agonist peptides of the invention are amidated at the C-terminal amino acid of the peptide. In still other embodiments, the FGF18 agonist peptides of the invention are acylated at the N-terminal amino acid of the peptide and are amidated at the C-terminal amino acid of the peptide.

FGF18 agonist peptides of the invention are made in a variety of ways. In one aspect, the FGF18 agonist peptides are synthesized by solid phase synthesis techniques including those described in Merrifield, J. Am. Chem. Soc., 85, 2149 (1963); Davis et al., Biochem. Intl., 10, 394-414 (1985); Larsen et al., J. Am. Chem. Soc., 115, 6247 (1993); Smith et al., J. Peptide Protein Res., 44, 183 (1994); O'Donnell et al., J. Am. Chem. Soc., 118, 6070 (1996); Stewart and Young, Solid Phase Peptide Synthesis, Freeman (1969); Finn et al., The Proteins, 3.sup.rd ed., vol. 2, pp. 105-253 (1976); and Erickson et al., The Proteins, 3.sup.rd ed., vol. 2, pp. 257-527 (1976). The invention contemplates synthetic FGF18 agonist peptides. Alternatively, the FGF18 agonist peptide is expressed recombinantly by introducing a nucleic acid encoding an FGF18 agonist peptide of the invention into host cells, which are cultured to express the peptide. Such FGF18 agonist peptides are purified from the culture media or cell pellets.

While not wishing to be bound by theory, the present disclosure is based at least in part on the design of FGF18 agonist peptides, which function to inhibit, decrease, or eliminate hair and/or hair growth when applied to a target location in a subject. Described herein are methods for decreasing, inhibiting, or eliminating hair and/or hair growth, and related pharmaceutical, veterinary and/or cosmetic preparations or compositions.

Topical Compositions

Any of the FGF18 agonist peptides (or peptide complexes) of the invention or nucleic acids encoding the FGF18 agonist peptides described herein may be provided in a composition (e.g., a pharmaceutical or cosmetic composition). In this regard, the FGF18 agonist peptide (or peptide complex) is formulated with a physiologically-acceptable (i.e., pharmacologically-acceptable) carrier, buffer, excipient, or diluent, as described further herein. Optionally, the FGF18 agonist peptide is in the form of a physiologically acceptable salt, which is encompassed by the invention. "Physiologically acceptable salts" means any salts that are pharmaceutically acceptable. Some examples of appropriate salts include acetate, hydrochloride, hydrobromide, sulfate, citrate, tartrate, glycolate, and oxalate. If desired, the composition comprises one or more additional pharmaceutically-effective agents.

Embodiments disclosed herein are directed to topical compositions comprising an effective amount of a FGF18 agonist peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, PEPTIDE NO: 15, and combinations thereof, and a cosmetically acceptable excipient.

In certain embodiments, the effective amount of FGF18 agonist peptide is about 0.00001% to about 1% w/w, about 0.0001% to about 1% w/w, about 0.001% to about 1% w/w, about 0.01% to about 1% w/w, or about 0.1% to about 1% w/w of the final composition. In certain embodiments, the effective amount of FGF18 agonist peptide is about 0.0001% w/w of the final composition. In certain embodiments, the effective amount of FGF18 agonist peptide is about 0.001% w/w of the final composition. In certain embodiments, the effective amount of FGF18 agonist peptide is about 0.01% w/w of the final composition.

In certain embodiments, the effective amount of FGF18 agonist peptide is about 1 ng/ml to about 100 ng/ml, about 10 ng/ml about 90 mg/ml, about 20 ng/ml to about 80 ng/ml, about 30 ng/ml to about 70 ng/ml, or about 40 ng/ml to about 60 ng/ml in the final composition. In certain embodiments, the effective amount of FGF18 agonist peptide is about 1 ng/ml in the final composition. In certain embodiments, the effective amount of FGF18 agonist peptide is about 10 ng/ml in the final composition. In certain embodiments, the effective amount of FGF18 agonist peptide is about 100 ng/ml in the final composition.

In certain embodiments, the effective amount of FGF18 agonist peptide is about 1 µM to about 10 µM, about 2 µM about 9 µM, about 3 µM to about 8 µM, about 4 µM to about 7 µM, or about 5 µM to about 6 µM in the final composition. In certain embodiments, the effective amount of FGF18 agonist peptide is about 1 µM in the final composition. In certain embodiments, the effective amount of FGF18 agonist peptide is about 5 µM in the final composition. In certain embodiments, the effective amount of FGF18 agonist peptide is about 10 µM in the final composition.

In certain embodiments, the effective amount of FGF18 agonist peptide is about 0.01 µg to about 1000 µg, about 0.1 µg to about 100 µg, about 1 µg to about 10 µg, about 2 µg to about 8 µg, or about 3 µg to about 5 µg in the final composition. In certain embodiments, the effective amount of FGF18 agonist peptide is about 0.1 µg in the final composition. In certain embodiments, the effective amount of FGF18 agonist peptide is about 1 µg in the final composition. In certain embodiments, the effective amount of FGF18 agonist peptide is about 10 µg in the final composition.

In certain embodiments, the topical composition comprises an effective amount of FGF18 agonist peptide comprising the amino acid sequence KQLR (SEQ ID NO:1). In certain embodiments, the topical composition comprises an effective amount of FGF18 agonist peptide comprising the amino acid sequence RTGQYK (SEQ ID NO: 2). In certain embodiments, the topical composition comprises an effective amount of FGF18 agonist peptide comprising the amino acid sequence DRLK (SEQ ID NO:3). In certain embodiments, the topical composition comprises an effective amount of FGF18 agonist peptide comprising the amino acid sequence EKTD (SEQ ID NO:4). In certain embodiments, the topical composition comprises an effective amount of FGF18 agonist peptide comprising the amino acid sequence EKDD (SEQ ID NO:5). In certain embodiments, the topical composition comprises an effective amount of FGF18 agonist peptide comprising the amino acid sequence KRTG (SEQ ID NO: 6). In certain embodiments, the topical composition comprises an effective amount of FGF18 agonist peptide comprising the amino acid sequence EKND (SEQ ID NO: 7). In certain embodiments, the topical composition comprises an effective amount of FGF18 agonist peptide comprising the amino acid sequence DRDE (SEQ ID NO: 8). In certain embodiments, the topical composition comprises an effective amount of FGF18 agonist peptide comprising the amino acid sequence DKSE (SEQ ID NO:9). In certain embodiments, the topical composition comprises an effective amount of FGF18 agonist peptide comprising the amino acid sequence DRVE (SEQ ID NO:10). In certain embodiments, the topical composition comprises an effective amount of FGF18 agonist peptide comprising the amino acid sequence DRTD (SEQ ID NO:11). In certain embodiments, the topical composition comprises an effective amount of FGF18 agonist peptide comprising the amino acid sequence IEKV (SEQ ID NO:12). In certain embodiments, the topical composition comprises an effective amount of FGF18 agonist peptide comprising the amino acid sequence DRV (PEPTIDE NO:15).

In certain embodiments, the FGF18 agonist peptide of the topical composition has at its N-terminal a protection group selected from the group consisting of acetyl group, fluorenyl methoxy carbonyl group, formyl group, palmitoyl group, myristyl group, stearyl group, linoleate group, polyethylene glycol (PEG), or other cosmetically acceptable protecting groups.

In certain embodiments, the FGF18 agonist peptides of the topical composition are acylated at the N-terminal amino acid of the peptide. In other embodiments, the FGF18 agonist peptides of the invention are amidated at the C-terminal amino acid of the peptide. In still other embodiments, the FGF18 agonist peptides of the invention are acylated at the N-terminal amino acid of the peptide and are amidated at the C-terminal amino acid of the peptide.

In some embodiments, topical composition comprises an effective amount of one or more FGF18 agonist peptides as described herein, and a cosmetically acceptable topical excipient. In some embodiments, the cosmetically acceptable topical excipient is selected from the group consisting of a diluent, a solvent, a surfactant, a thickening agent, a foaming agent, a gelling agent, an emulsifier, a water soluble vehicle, a hydrophobic vehicle, a viscosity modifier, an antioxidant, a buffer, a skin protectant, a chelating agent, a fragrance, a preservative, a surfactant, a lubricant, a penetration enhancer, a humectant, a moisturizer, a solubilizer, a plasticizer, a propellant, an alcohol, an emollient, and combinations thereof. The excipients described herein function to stabilize the FGF18 agonist peptides and compositions. In certain embodiments, the excipient does not comprise only water. In some embodiments, the cosmetically acceptable topical excipient is selected from the group consisting water, glycerin, sodium levulinate, and combinations thereof.

In additional embodiments, the topical composition is formulated as a lotion, cream, serum, spray, mousse, aerosol, emulsion, cake, ointment, gel, paste, patch, pencil, towelette, mask, stick, foam, elixir, oil-in-water emulsion (O/W), water-in-oil (W/O) emulsion, microemulsion, or concentrate.

In additional embodiments, the topical composition further comprises an agent selected from the group consisting of a lathering surfactant, a moisturizer, an anti-dandruff agent, a vitamin, a hydroxy acid, a chemical or physical sunscreen, an antioxidant, a retinoid, a progesterone, and combinations thereof.

In some embodiments, the topical composition is a foam. In some embodiments, the foam comprises a cosmetically acceptable topical excipient selected from the group consisting of a diluent, a solvent, a non-solvent, a volatile solvent, a residual solvent, surfactant, a thickening agent, a foaming agent, a gelling agent, an emulsifier, a water soluble (hydrophilic) vehicle, a hydrophobic vehicle, a viscosity modifier, an antioxidant, a buffer, a pH stabilizing agent, a skin protectant, a chelating agent, a fragrance, a surfactant, a lubricant, a penetration enhancer, a preservative, a humectant, a moisturizer, a solubilizer, a plasticizer, a propellant, an alcohol, an emollient, and combinations thereof. In some embodiments, the topical composition is a foam comprising an effective amount of a FGF18 agonist peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, PEPTIDE NO: 15, and combinations thereof, and a cosmetically acceptable topical excipient selected from one or more of a solvent, an emulsifier, a surfactant, and a propellant.

In some embodiments, the topical composition is a foam comprising an effective amount of a FGF18 agonist peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, PEPTIDE NO: 15, and combinations thereof, and a cosmetically acceptable topical excipient selected from one or more of propylene glycol, PEG 400, benzyl alcohol, ethanol, water, DMSO, PEG 4000, and PEG 3350.

In some embodiments, the topical composition is an ointment. In some embodiments, the ointment comprises a diluent, a solvent, a non-solvent, a volatile solvent, a residual solvent, surfactant, a thickening agent, a gelling agent, an emulsifier, a water soluble (hydrophilic) vehicle, a hydrophobic vehicle, a viscosity modifier, an antioxidant, a buffer, a pH stabilizing agent, a skin protectant, a chelating agent, a fragrance, a surfactant, a lubricant, a penetration enhancer, a preservative, a humectant, a moisturizer, a solubilizer, a plasticizer, an alcohol, an emollient, and a combination thereof. In some embodiments, the topical composition is an ointment comprising a an effective amount of a FGF18 agonist peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, PEPTIDE NO: 15, and combinations thereof, and a cosmetically acceptable topical excipient selected from one or more of a solvent, an emulsifier, and a surfactant.

In some embodiments, the topical composition is an ointment comprising an effective amount of a FGF18 agonist peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, PEPTIDE NO: 15, and combinations thereof, and a cosmetically acceptable topical excipient selected from one or more of propylene glycol, PEG 400, benzyl alcohol, ethanol, water, DMSO, PEG 4000, and PEG 3350.

In some embodiments, the topical composition is a gel. In some embodiments, the topical composition is an emulsified gel. In some embodiments, the emulsified gel comprises a cosmetically acceptable topical excipient selected from the group consisting of a gelling agent, a diluent, a solvent, a non-solvent, a volatile solvent, a residual solvent, surfactant, a thickening agent, a gelling agent, an emulsifier, a water soluble (hydrophilic) vehicle, a hydrophobic vehicle, a viscosity modifier, an antioxidant, a buffer, a pH stabilizing agent, a skin protectant, a chelating agent, a fragrance, a surfactant, a lubricant, a penetration enhancer, a preservative, a humectant, a moisturizer, a solubilizer, a plasticizer, an alcohol, an emollient, and a combination thereof. In some embodiments, the topical composition is an emulsified gel comprising an effective amount of a FGF18 agonist peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, PEPTIDE NO: 15, and combinations thereof, and a cosmetically acceptable topical excipient selected from one or more of a solvent, a skin protectant, an emulsifier, an antioxidant, a viscosity modifier, and a surfactant.

In some embodiments, the topical composition is a gel comprising an effective amount of a FGF18 agonist peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, PEPTIDE NO: 15, and combinations thereof, and a cosmetically acceptable topical excipient selected from one or more of propylene glycol, PEG 400, benzyl alcohol, ethanol, water, DMSO, PEG 4000, and PEG 3350, and hydroxypropyl cellulose.

In some embodiments, the topical composition is a solution. In some embodiments, the solution comprises a cosmetically acceptable topical excipient selected from a diluent, a solvent, a non-solvent, a volatile solvent, a residual solvent, surfactant, a thickening agent, a gelling agent, an emulsifier, a water soluble (hydrophilic) vehicle, a hydrophobic vehicle, a viscosity modifier, an antioxidant, a buffer, a pH stabilizing agent, a skin protectant, a chelating agent, a fragrance, a surfactant, a lubricant, a penetration enhancer, a preservative, a humectant, a moisturizer, a solubilizer, a plasticizer, an alcohol, an emollient, and a combination thereof. In some embodiments, the topical composition is a solution comprising an effective amount of a FGF18 agonist peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, PEPTIDE NO: 15, and combinations thereof, and a cosmetically acceptable topical excipient selected from one or more of a solvent, a surfactant, viscosity modifier, and a foaming agent. In some embodiments, the topical composition is a self-foaming solution comprising an effective amount of a FGF18 agonist peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, PEPTIDE NO: 15, and combinations thereof, and a cosmetically acceptable topical excipient selected from one or more of propylene glycol, PEG 400, benzyl alcohol, ethanol, water, DMSO, Transcutol P, Poloxamer 188, Kolliphor CS 20, Povidone K30, and HEC 250HX.

In some embodiments, the topical composition may include a surfactant selected from the group consisting of naturally-occurring phosphatides, for example, soy bean, lecithin, and esters or partial esters derived from fatty acids; hexitol anhydrides, for example sorbitan monooleate; condensation products of the said partial esters with ethylene oxide, for example polyoxyethylene sorbitan monooleate; polyethylene glycol dodecyl ether, such as that sold under the tradename, Brij® L4, or the like; polysorbate 80, such as that sold under the tradename Tween® 80; cetostearyl alcohol; polyoxyethylene stearyl ethers (steareth) such as that sold under the tradename Brij® S2 and S20, ceteareth-12-30, such as that sold under the tradename Cremaphor A25; cetearyl alcohol, ceteth 2-23, stearyl alcohol (Cremophor A6); sorbitan sesquioleate, such as that sold under the tradename Span™ 83; cetomacrogol 1000, glycerol monostearate; PEG stearates; polyoxyl castor oils, such as that sold under the tradename Kolliphor EL and RH40; stearic acid; apricot kernel oil PEG-6 esters such as that sold under the tradename Labrafil M1944CS; hydrogenated castor oil; a polyethylene glycol ether of cholesterol (choleth-24); glyceryl monoesters, such as glyceryl stearate, palmitate and oleate; myristyl alcohol; polyethylene glycol nonyl phenyl ether; polyoxyethylene octyl phenyl ether; octyldodecanol; PEG/glycol stearate; propylene glycol stearate; a poloxamer such as that sold under the tradename Poloxamer 188, Kolliphor CS 20; and combinations thereof. In some embodiments, the surfactants may function as emulsifiers.

In some embodiments, the emulsifier is in an amount of about 0.1% w/w to about 40% w/w. In some embodiments, the emulsifier is in an amount of about 0.1% w/w to about 30% w/w, about 0.1% w/w to about 20% w/w, about 0.1% w/w to about 10% w/w, about 1% w/w to about 40% w/w, about 1% w/w to about 30% w/w, about 1% w/w to about 20% w/w, about 1% w/w to about 10% w/w, or a value within any of the ranges or a range between any two of these values.

In some embodiments, the topical composition may include a penetration enhancer selected from the group consisting of water; propylene glycol; an alcohol; dimethyl sulfoxide (DMSO); diethylene glycol monoethyl ether, such as that sold under the tradename Transcutol P or Transcutol HP (highly purified); isopropyl myrisate; diisopropyl adipate; dimethyl isosorbide, such as that sold under the tradename Super Refined Arlasolve DMI; oleyl alcohol; oleic acid; isostearic acid; glycerin; surfactants such as polysorbate 80; terpenes such as alpha-terpineol; sodium levulinate; and combinations thereof.

In some embodiments, the penetration enhancer is in an amount of about 1% w/w to about 50% w/w, about 1% w/w to about 40% w/w, about 1% w/w to about 30% w/w, about 1% w/w to about 20% w/w, about 1% w/w to about 10% w/w, about 5% w/w to about 50% w/w, about 5% w/w to about 40% w/w, about 5% w/w to about 30% w/w, about 5% w/w to about 20% w/w, about 5% w/w to about 10% w/w, or a value within any of the ranges or a range between any two of these values.

In some embodiments, the topical composition may include a skin protectant having an oil phase. In some embodiments, the oil phase is selected from the group consisting of a mineral oil such as liquid paraffin, sunflower oil, soya bean oil, a vegetable oil, for example, *arachis* oil, almond oil, castor oil and castor oil hydrogenated, olive oil, sesame oil or coconut oil, polyorganosiloxane, such as polydimethylsiloxane, such as that sold under the tradename Dimethicone 350, cyclomethicone, a PEGylated oil for example apricot kernel oil PEG-6 esters, a synthetic triglyceride for example caprylic/capric/stearic triglyceride, such as that sold under the tradename Captex, diisopropyl adipate, a glyceryl monoester for example glyceryl oleate and glyceryl palmitate a fatty acid ester, for example isopropyl isostearate, isopropyl palmitate and isopropyl myristate, a aliphatic alcohol, for example isostearyl alcohol, a long chain fatty alcohol, such as octyldodecanol, a stearyl ether, such as polypropylene glycol-11 stearyl ether and polypropylene glycol-15 stearyl ether, propylene glycol stearate and a combination thereof.

In some embodiments, the skin protectant is in an amount of about 1% w/w to about 97% w/w.

In some embodiments, the topical composition may include a solvent which may be selected from the group consisting of water, glycerin, propylene glycol, dipropylene glycol, polyethylene glycol having a molecular weight of about 200 to about 8000, an alcohol, dimethyl sulfoxide (DMSO), diethylene glycol monoethyl ether, such as that sold under the tradename Transcutol P or Transcutol HP (highly purified), and combinations thereof.

In some embodiments, the solvent comprises propylene glycol, PEG 400, super refined (SR) PEG 400, benzyl alcohol, ethanol, water, glycerin, DMSO, Transcutol P, Transcutol HP, or combinations thereof. In some embodiments, the solvent is in an amount of about 0.5% w/w to about 70% w/w.

In some embodiments, the topical composition may include a viscosity modifier which may be selected from the group consisting of a carbomer for example carbomer homopolymer or copolymer that contains a block copolymer of polyethylene glycol and a long chain alkyl acid ester, such as that sold under the tradename Carbopol® Ultrez 10; beeswax; microcrystalline wax; a hard or soft paraffin; a cetyl alcohol; lanolin alcohols; a polyvinylpyrrolidone, such as Povidone K30 or copolymer thereof such as povidone acrylate copolymer; a cellulose derivative such as hydroxypropyl cellulose (HPC); a natural based polymer such as xanthan gum; Sepineo P600 an acrylamide/sodium acryloyldimethyl taurate copolymer/isohexadecane; glycerin; polyethylene glycol having a molecular weight of about 200 to about 8000; sodium hyaluronate; and combinations thereof.

In some embodiments, the viscosity modifier is in an amount of about 0.25% w/w to about 82% w/w.

In some embodiments, the foaming agent comprises one or more poloxamers, such as that sold under the tradename Poloxamer 188; Kolliphor CS 20; PEG caprylic/capric triglycerides; cocamidopropyl betaine; or lauric diethanolamide. In some embodiments, the foaming agent is in an amount of about 0.1% w/w to about 35% w/w, about 0.1% w/w to about 30% w/w, about 0.1% w/w to about 25% w/w, about 1% w/w to about 35% w/w, about 1% w/w to about 25% w/w, or a range of any two of these values, or a value within any of the foregoing ranges.

In some embodiments, the topical composition may include a polyethylene glycol having a molecular weight of about 200 to about 8000 and is selected from the group consisting of PEG 200, PEG 300; PEG 400; PEG 540; PEG 600; PEG 900; PEG 1450; PEG 1500; PEG 2000, PEG 4000, PEG 3350, PEG 6000, PEG 8000, or a combination thereof. In some embodiments, the polyethylene glycol having a molecular weight of about 200 to about 8000 is selected from the group consisting of PEG 400, PEG 4000, PEG 3350 or combinations thereof. In some embodiments, the polyethylene glycol having a molecular weight of about 200 to about 8000 is labeled as "super refined."

In some embodiments, the topical composition may include an alcohol selected from the group consisting of benzyl alcohol, ethanol, isopropyl alcohol, phenoxyethanol, fatty alcohols such as cetyl alcohol and a combination thereof.

In some embodiments, the alcohol is in an amount of about 1% w/w to about 100% w/w. In some embodiments, the alcohol is in an amount of about 30%.

In some embodiments, the topical composition may include a propellant may be selected from the group consisting of 1,1,1,2-tetrafluoroethane (HFA-134a), hydrocarbon-based, hydrocarbon blends, dimethyl ether, hydrofluorocarbons, nitrogen, n-butane, isobutene, propane, carbon dioxide; trans-1,3,3,3-tetrafluoroprop-1-ene (HFO-1234ze) or a combination thereof.

In some embodiments, the propellant is in an amount of about 3% w/w to about 30% w/w.

In some embodiments, the topical composition may include an antioxidant selected from butylated hydroxytoluene (BHT), butylated hydroxyanisole (BHA), propyl gallate, acorbic acid, acscorbyl palmitate, α-tocopherol including other stabilisers such as EDTA, citric acid, or a combination thereof.

In some embodiments, the antioxidant is in an amount of about 0.001% w/w to about 5.2% w/w.

In additional embodiments, the topical composition further comprises an agent selected from the group consisting of a lathering surfactant, a moisturizer, an anti-dandruff agent, a vitamin, a hydroxy acid, a chemical or physical sunscreen, an antioxidant, a retinoid, and a progesterone.

Accordingly, the FGF18 agonist peptide or topical compositions described herein can be provided as a topical composition using routine methods, i.e., a preparation may be formulated in accordance with conventional pharmaceutical or cosmetic practice with pharmaceutical or cosmetic excipients conventionally used for topical applications. The nature of the vehicle employed in the preparation of any particular composition will depend on the method intended for administration of that composition.

A topical composition described herein may be formulated in a variety of product forms, such as a lotion, cream, serum, spray, aerosol, emulsion, cake, ointment, essence, gel, mousse, paste, patch, pencil, towelette, mask, stick, foam, elixir, concentrate, and the like. The preparations can include one or more of: a solvent, an emulsifier, an emollient, a slip aid (e.g., a silicone), a humectant, a fragrance, a pigment or coloring, a preservative, a surfactant, a thickener, a sequestering agent, a wax, an oil, a gelling agent, a pearlising agent, a pH adjusting agent. Acceptable vehicles include water (e.g., deionized water); oils such as vegetable oils or mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; polyethylene glycols; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

In preferred embodiments, the topical composition comprises an effective amount of a FGF18 agonist peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, PEPTIDE NO: 15, and combinations thereof, glycerin, water, and sodium levulinate.

In preferred embodiments, the topical composition comprises about 0.001% to about 1% w/w of a FGF18 agonist peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, PEPTIDE NO: 15, and combinations thereof, about 35% to about 65% w/w glycerin, about 30% to about 60% w/w water, and about 2% to about 10% w/w sodium levulinate of the topical composition.

In preferred embodiments, the topical composition comprises about 0.01% w/w of a FGF18 agonist peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, PEPTIDE NO: 15, and combinations thereof, about 50% w/w glycerin, about 44% w/w water, and about 6% w/w sodium levulinate of the topical composition.

Methods of Treatment and Methods of Use

Embodiments herein are directed to a method of decreasing, or eliminating hair or hair growth in a subject comprising topically administering to a target location a topical composition comprising an effective amount of one or more FGF18 agonist peptide as described herein, or a topical composition as described herein.

Some embodiments are directed to a method of modulating a hair follicle-mediated function (e.g. FGF18) in a subject comprising topically administering to a target location a topical composition comprising an effective amount of one or more FGF18 agonist peptide as described herein, or a topical composition as described herein. In certain embodiments, the FGF18 agonist peptide induces a regressive hair follicle catagen phase, or prevents the hair follicle from entering anagen phase, which produces a decrease or suppression of hair growth. In certain embodiments, the FGF18 agonist peptide induces or prolongs a quiescent hair follicle state (telogen), which produces a decrease in hair growth. In certain embodiments, the FGF18 agonist peptide both induces the catagen phase and induces or prolongs the telogen hair follicle state. In certain embodiments, the FGF18 agonist prevents the telogen to anagen transition suppressing growth of the hair from the follicle.

Embodiments herein also relate to methods for decreasing, diminishing, or suppressing hair growth in a subject comprising topically administering to the target location a topical composition comprising an effective amount of one or more FGF18 agonist peptides as described herein, or a topical composition as described herein.

Embodiments herein also relate to methods for eliminating, retarding, or suppressing hair growth in a subject comprising topically administering to the target location a topical composition comprising an effective amount of one or more FGF18 agonist peptides as described herein, or a topical composition as described herein.

Embodiments herein also relate to methods for increasing the time period between the removal of hair by depilation or shaving in a subject comprising topically administering to the target location a topical composition comprising an effective amount of one or more FGF18 agonist peptides as described herein, or a topical composition as described herein.

Embodiments herein also relate to methods for minimizing the appearance of hair in a subject comprising topically administering to the target location a topical composition comprising an effective amount of one or more FGF18 agonist peptides as described herein, or a topical composition as described herein.

Embodiments herein also relate to methods for improving skin appearance in a subject comprising topically administering to the target location a topical composition comprising an effective amount of one or more FGF18 agonist peptides as described herein, or a topical composition as described herein.

In certain embodiments, the improvement in the skin appearance is a reduction in hair growth or improvement in skin smoothness.

In certain embodiments, the effective amount of FGF18 agonist peptide is about 0.00001% to about 1% w/w, about 0.0001% to about 1% w/w, about 0.001% to about 1% w/w, about 0.01% to about 1% w/w, or about 0.1% to about 1% w/w of the final composition. In certain embodiments, the effective amount of FGF18 agonist peptide is about 0.0001% w/w of the final composition. In certain embodiments, the effective amount of FGF18 agonist peptide is about 0.001% w/w of the final composition. In certain embodiments, the effective amount of FGF18 agonist peptide is about 0.01% w/w of the final composition.

In certain embodiments, the effective amount of FGF18 agonist peptide is about 1 ng/ml to about 100 ng/ml, about 10 ng/ml about 90 mg/ml, about 20 ng/ml to about 80 ng/ml, about 30 ng/ml to about 70 ng/ml, or about 40 ng/ml to about 60 ng/ml in the final composition. In certain embodiments, the effective amount of FGF18 agonist peptide is about 1 ng/ml in the final composition. In certain embodiments, the effective amount of FGF18 agonist peptide is about 10 ng/ml in the final composition. In certain embodiments, the effective amount of FGF18 agonist peptide is about 100 ng/ml in the final composition.

In certain embodiments, the effective amount of FGF18 agonist peptide is about 1 µM to about 10 µM, about 2 µM about 9 µM, about 3 µM to about 8 µM, about 4 µM to about 7 µM, or about 5 µM to about 6 µM in the final composition. In certain embodiments, the effective amount of FGF18 agonist peptide is about 1 µM in the final composition. In certain embodiments, the effective amount of FGF18 agonist peptide is about 5 µM in the final composition. In certain embodiments, the effective amount of FGF18 agonist peptide is about 10 µM in the final composition.

In certain embodiments, the effective amount of FGF18 agonist peptide is about 0.01 µg to about 1000 µg, about 0.1 µg to about 100 µg, about 1 µg to about 10 µg, about 2 µg to about 8 µg, or about 3 µg to about 5 µg in the final composition. In certain embodiments, the effective amount of FGF18 agonist peptide is about 0.1 µg in the final composition. In certain embodiments, the effective amount of FGF18 agonist peptide is about 1 µg in the final composition. In certain embodiments, the effective amount of FGF18 agonist peptide is about 10 µg in the final composition.

In embodiments described herein, the hair to be removed, eliminated, slowed, decreased, or suppressed is selected from the group consisting of scalp hair, facial hair, body hair, eyebrows, pubic hair, back hair, leg hair, arm hair, upper lip hair, chin hair, and combinations thereof.

In some embodiments, the FGF18 agonist peptide or topical compositions described herein may be administered directly to the target location, including skin, or localized areas of the skin with undesired or excessive amounts of hair (e.g., any skin surface with hair), without applying it in any substantial amount to undesired topical locations.

In some embodiments, the FGF18 agonist peptide or topical compositions described herein are administered to the target location without any preparation of the skin or hair. In some embodiments, the FGF18 agonist peptide or topical compositions described herein are administered to the target location after the hair has been removed using another method such as shaving, waxing, plucking, treading, electrolysis, the use of depilatory creams, the use of a laser, or combinations thereof. In some embodiments, the FGF18 agonist peptide or topical compositions described herein are administered to the target location after the skin has been cleaned, exfoliated, moisturized, or treated with another topical composition.

In some embodiments, the FGF18 agonist peptide or topical compositions described herein are administered to the target location using the subject's hands. In some embodiments, the FGF18 agonist peptide or topical compositions described herein are administered to the target location using a gloved hand. In some embodiments, the FGF18 agonist peptide or topical compositions described herein are administered to the target location using a tool, such as a sponge, a cotton ball, a swab, a spatula, a tongue depressor, a brush, roll-on/rollerball, applicator tip, an adhesive patch, or combinations thereof.

In some embodiments, after the FGF18 agonist peptide or topical compositions described herein are administered to the target location, the treated target location is then treated with a phototherapy device. In certain embodiments, the phototherapy is used for 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, or 30 minutes.

In some embodiments, the FGF18 agonist peptide or topical compositions described herein can be administered to the subject once (e.g., as a single application). In some embodiments, the FGF18 agonist peptide or topical compositions described herein can be administered at least once daily, at least twice daily, at least three times daily, at least four times daily, or on "as needed" basis to maintain the desired effect. In some embodiments, the FGF18 agonist peptide or topical compositions described herein may be administered daily, weekly, twice weekly, every two weeks, every three weeks, monthly, as needed. Alternatively, these topical compositions can be applied to the target location less frequently, i.e., from 1 to 5 times a week. In one embodiment, the FGF18 agonist peptide or the topical composition can be applied topically to the target location at least once per day for at least three weeks, four weeks, twelve weeks or longer, e.g., indefinitely. The FGF18 agonist peptide or topical compositions described herein may be administered at any interval to achieve the desired effect, e.g. reduction of hair growth. In some embodiments, the FGF18 agonist peptide or topical compositions described herein may be administered to a subject for a period of 1, 2, 3, 4, 5, 6, 7 days, about a week, about two weeks, about three weeks, about four weeks, about five weeks, about six weeks, about two months, about three months, about four months, about five months, about six months, or a range of any two of these values. In some embodiments, treatment may be continued for at least a week, a month, or a year. In some embodiments, treatment may extend over multiple years, until hair has been eliminated, or the lifetime of the subject.

In additional embodiments, the methods further comprise administering a second skin care composition to the target location after any of the FGF18 agonist peptides or topical composition comprising any of the FGF18 agonist peptides as described herein, is applied.

Kits

Some embodiments are also directed to any of the FGF18 agonist peptide or topical compositions described herein in a kit. In some embodiments, the kit may comprise ampoules, disposable syringes, capsules, vials, tubes, or the like. In some embodiments, the kit may comprise a single dose container or multiple dose containers comprising the topical composition of embodiments herein. In some embodiments, each dose container may contain one or more unit doses. In some embodiments, the kit may include an applicator. In some embodiments, the kit may include the topical composition of embodiments herein in a tube having an applicator tip (e.g. a "pen"). In some embodiments, the kits include all equipment needed for combination therapy (e.g. vials of the topical composition of embodiments herein and a phototherapy device; tubes of the FGF18 agonist peptide or topical compositions described herein and tubes having a applicator tip containing a second FGF18 agonist peptide or topical compositions described herein; or tubes of a topical composition of embodiments herein and a second active ingredient/agent). In some embodiments, the kit further includes a phototherapy device. In some embodiments, the kit further includes an abrading device. In some embodiments, the kit contains all necessary equipment for a treatment course (e.g., 7 days of treatment). For example, the topical composition may be a liquid, for example a homogeneous liquid or a suspension, sold in a bottle which dispenses the FGF18 agonist peptide or topical compositions described herein as drops or a liquid film (for example from an applicator tip that contacts a target area of the skin to dispense the compound substantially only on a target area of the skin to be treated). In one embodiment, the kit includes the FGF18 agonist peptide or topical compositions described herein in a gel or ointment, sold in a tube. In another embodiment, the FGF18 agonist peptide or topical compositions described herein is provided in a viscous liquid (such as carboxylmethylcellulose, hydroxypropylmethycellulose, polyethylene glycol, glycerin, polyvinyl alcohol, or oil containing drops) for rubbing into the skin. The FGF18 agonist peptide or topical compositions described herein may have preservatives or be preservative-free (for example, in a single-use container).

In some embodiments the FGF18 agonist peptide or topical compositions described herein can be applied topically using an applicator device. In some embodiments, a kit further includes an applicator device. In some embodiments, the applicator device permits application of the composition to a target site on the skin while preventing the composition from contacting non-target site areas of the skin. In some embodiments, the applicator device may allow the composition to be applied without first applying the composition to one's fingers. In some embodiments, the applicator device may include gloves, sponges, spatulas, swabs, syringes without needles, adhesive patches, or a combination thereof. In some embodiments, use of spatulas or swabs, or the like may require the device to be inserted into a container containing the composition. In some embodiments, use of syringes or adhesive patches may be accomplished by filling the syringe or patch with the composition. The FGF18 agonist peptide or topical compositions described herein may be expelled from the syringes onto the person's skin and/or may be topically spread on the skin by the spatulas or swabs.

In some embodiments, the FGF18 agonist peptide or topical compositions described herein is administered in conjunction, adjunctively or concomitantly, with a biologically active agent in a topical sunscreen agent.

In some embodiments, the FGF18 agonist peptide or topical compositions described herein is administered in conjunction, adjunctively or concomitantly, with phototherapy, natural sunlight, ultraviolet light exposure, or combinations thereof Combinations The FGF18 agonist peptides or topical compositions described herein may also be utilized in combination with other active compounds, vitamins (such as vitamin A, vitamin B3, vitamin B5, and vitamin B12, vitamin C, vitamin K, vitamin E and mixtures thereof); hydroxy acids (such as glycolic acid, lactic acid, malic acid, salicylic acid, citric acid, and tartaric acid); chemical and physical sunscreens (e.g., Mexoryl®, avobenzene, octinoxate, octisalate, oxybenzone, titanium dioxide, zinc oxide); antioxidants (e.g., sulfhydryl compounds and their derivatives such as sodium metabisulfite and N-acetyl-cysteine, lipoic acid and dihydrolipoic acid, resveratrol, lactoferrin, and ascorbic acid and ascorbic acid derivatives, butylated hydroxytoluene); retinoids such as retinol and retinyl palmitate; tocopherols and their esters; progesterones and naturally-derived ingredients with progesterone-like activity; anti-dandruff agents such as coal tar or ketoconazole; peptides such as palmitoyl pentapapeptide (Matrixyl®). Such additional agents may be provided separately from an FGF18 agonist peptide composition described herein or may be present in the same preparation, e.g., in an amount from about 0.001% to about 10% by weight, in particular in an amount from about 0.01% to about 5% by weight.

EXAMPLES

Example 1: Identification and Characterization of FGF Agonists

The hair follicle (HF) is a self-renewing "mini-organ" which undergoes continuous cycles of growth and regression, following a precise scheme in which a complex and fine-tuned interaction of signals induces deep metabolic and morphologic changes. The HF cycle is divided in an active growth phase (anagen), a regressive phase (catagen) and a final quiescence state (telogen). Epithelial FGF18 is responsible for regulating the hair cycle through the non-growth phases although the transition from the growth phase to the quiescent phase is not yet fully understood. Different strategies have been utilized in order to establish and validate an experimental approach to assess the mechanism of FGF18 agonists. One strategy is to block anagen at a point where FGF18 analogues should block the transition from telogen to anagen preventing cycle restart. Another strategy involves evaluating the expression of FGF receptor 3 during telogen based on the rationale that exposure to FGF18 could induce over expression of its receptor FGFR3. Yet another strategy is to establish a regressive HF in vitro forced involution model to elucidate the molecular mechanism underlying the quiescence state of HF and to develop tools for screening active compounds.

FGF18 regulates hair follicle or epidermal stem cells. Theoretically, FGF18 itself or any other substance that exerts FGF18-like activity—e.g. FG18 agonists—are expected to be useful as a safe and effective hair-growth suppressing agent in a cosmetic or other topical composition. Described herein are a number of FGF18 agonist peptides and compositions that decrease, reduce, or suppress hair growth.

While not wishing to be bound by theory, it is believed that FGF18 exerts an agonist effect on its putative cognate receptors FGFR1 and FGFR3, in skin and hair follicles. To design agonist peptides, the interaction of FGF18 residues with its proposed cognate receptors was evaluated.

Several 3D structures of FGF alone or complexed with Ig domains of FGFR have been published.

The structures in Table 3 were used to build models for FGF18-FGFR1 and FGF18-FGFR3 by performing structure and sequence alignments: FGF18 and FGF1 from both complexes FGF1-FGFR1 and FGF1-FGFR3. This modeling was achieved using the module Biopolymer:Align Structures By Homology in the Sybyl Package (Certara, USA).

TABLE 3

| 3D structures of FGF/FGFR Protein names |
|---|
| FGF2-FGFR1 |
| FGF1-FGFR1 |
| FGF1-FGFR3 |
| FGFR3 |
| FGF18 |

Based on FGF18-FGFR1 and FGF18-FGFR3 models, the interaction areas —H bonds, ionic and lipophilic interactions were identified. Residues from FGF18 interacting with the receptors were selected as potential agonist peptides. Furthermore, key residues on the receptors were also isolated and peptides were designed to complement these "hot spots". As FGF1 and FGF2 interact at least with FGFR1, they were aligned—based on their structure and sequence—with FGF18 to derive putative agonist peptides. Peptides were built with the Biopolymer module.

Ligand-Based Approach

Agonist peptides targeting FGFR1 and FGFR2, the latter, based on interaction analysis with FGF8, have been published. These sequences are publicly available and were subjected to pairwise sequence alignment to identify shorter common/conserved amino acid sequences. The pairwise alignment was performed with ClustalW as implemented in the database provided from the website found at https://npsa-prabi.ibcp.fr/(J. Comput. Aided Mol. Des. 2007, 21, 281-306). Peptides of at least 3 residues were identified—preferably larger for selectivity—and between 2 identical or strongly similar residues. Residues aligned with more than one gap were not considered.

Docking of Peptides on Receptors

Docking analysis involved positioning a ligand into the binding site of a protein and estimating the affinity of the ligand-protein complex with a score based on parameters taking into account the atom types, geometry and types of interactions.

For these analyses, FGFR1 & FGFR3 models were "calibrated" for virtual screening using known agonist peptides of smallest size. Surflex-dock was utilized for the docking and virtual screening. Peptides with a calculated affinity score "better" than the reference peptides were selected for final testing.

A final visual inspection was carried out on best-scored molecules to discard putative "false positives"—e.g. too constrained or unlikely conformations, "unreasonable" interaction patterns . . . —that were not detected by the software. Priority was given to peptides with shorter length.

Ligand-Based Screening

Peptidic ligands interacting with FGFR were aligned to derive novel peptides that may exert similar agonist effect of FGF18. The results are shown in Tables 4A and 4B below. Peptides that showed up several times are highlighted in bold. In some cases, no common residues could be found—shown as solid black cells.

TABLE 4A

Pairwise alignment of peptides mimicking FGF

|  | HFKDPKRL YCK | KTGPGQ KAIL | FLPMS AKS | ANRYLAMKEDG RLLAS | WYVALKRTG QYKLG | AKTV KFK |
|---|---|---|---|---|---|---|
| HFKDPKRL YCK |  | PGQK | MSAK | MKEDGRL | FKDPKR | KRLYC K |
| KTGPGQKA IL | PKR |  | PMSAK S | QKAIL | GQKAI | QKAIL |
| FLPMSAKS | LYCK | PGQKA |  | FLPM | FLPM | MSAK |
| ANRYLAMK EDGRLLAS | FKDPKRL | EDGRLL | YLAM |  | YLAMKEDGR | RYLA MK |
| WYVALKRT GQYKLG | YVALKR | GQYKL | YVAL | YVALKRTGQ |  | RTGQ YK |
| AKTVKFK | KTVKFK | KTVKF | VKFK | KTVKFK | KTVKFK |  |
| IEKVLENNY T | ENNY |  | IEKVLE N | EKVLEN | NNYT | KVLE |
| QLRLY | QLRLY | QLRL | LRL | LRL | LRLY | LRL |
| RTSG |  | RTSG |  | RTSG | RTSG |  |
| TFGS |  |  | TFGS |  | TFGS |  |
| DRVE | DRVE | DRV |  | DRVE |  |  |
| PYSSTA |  | PYSST | PYSSTA | YSS |  |  |
| SIDRV | IDRV |  | IDR | SIDRV | SIDR |  |

TABLE 4B

Pairwise alignment of peptides mimicking FGF

|  | IEKVLENNYT | QLRLY | RTSG | TFGS | DRVE | PYSSTA | SIDRV |
|---|---|---|---|---|---|---|---|
| HFKDPKRLYCK | KRLY | HFRLY |  |  | DRLK |  | FKDRL |
| KTGPGQKAIL |  | QKAI | KTGP G |  | QKAI | PGQKA |  |
| FLPMSAKS | FLPMSAK | LPM |  | PMSA |  | PMSAK S | MSAK |
| ANRYLAMKEDG RLLAS | NRYLED | MRL | KEDG |  | NRM K | YLA | AMDGR L |
| WYVALKRTGQY KLG | GQYK | LKQY | KRTG | ALGQ |  |  | ALKR |
| AKTVKFK | KTVK | VKF |  |  |  |  |  |
| IEKVLENNYT |  | LENNY |  |  | EKVL E |  | IEKV |
| QLRLY | LRLY |  |  |  | QLRL |  | LRL |
| RTSG |  |  |  |  |  |  |  |
| TFGS |  |  |  |  |  |  | FGS |

TABLE 4B-continued

Pairwise alignment of peptides mimicking FGF

|       | IEKVLENNYT | QLRLY | RTSG | TFGS | DRVE | PYSSTA | SIDRV |
|-------|------------|-------|------|------|------|--------|-------|
| DRVE  | DRVE       | DRV   |      |      |      |        | DRV   |
| PYSSTA|            |       |      | YSS  |      |        |       |
| SIDRV | IDRV       | IDRV  |      |      | DRV  |        |       |

The peptides identified in Tables 4A and 4B were docked on FGFR1 and FGFR3 to prioritize those to be synthesized and further characterized.

Protein-Based Screening

Building FGFR Models

FGF 18 interacts with FGFR1 and FGFR3 to exert its effect on hair follicles. To model the FGF18-FGFR1 complex, FGF1-FGFR1 and FGF2-FGFR1 complexes were utilized—PDBid respectively 1evt and 1cvs. The 2 complexes were superimposed according to FGFR1, then overlaid FGF 18-PDBid 4cjm—with FGF2 because the homology was better than with FGF1. The result showed residues of FGFR1 making hydrogen bonds or ionic interactions with the 3 FGF are: ALA167, ARG250, ASP282, GLN284, PRO285, HIS286, THR313, ALA314, VAL316 and ASP320.

Likewise, FGF18-FGFR3 was modeled with FGF1-FGFR3-PDBid 1ry7. FGF2 was extracted from 1cvs and superimposed to FGF1 of FGF1-FGFR3, then overlaid FGF 18-PDBid 4cjm—with FGF2 because the homology was better than with FGF1. The result illustrated that; residues of FGFR3 making hydrogen bonds or ionic interactions with the 3 FGF include: LYS161, ALA165, ARG248, VAL277, SER279, ASP280, HIS284, LYS319, GLU320, LEU321, GLU322, GLY342, ASN343 and SER344.

By observing the "contacts" of FGF1, 2 & 18 and FGFR1 & 3, several residues that are in close interaction were identified. Peptides consisting of these amino acids may exert a similar effect on FGFR as their cognate FGF ligands. Sequences of at least 3 residues were retained—for selectivity sake—and making at least 2 direct interactions with the receptors (Table 5). Peptides with 3 interactions are highlighted in bold.

TABLE 5

Peptides from the analysis of FGF-FGFR interactions

|       | FGF1              | FGF2              | FGF18                  |
|-------|-------------------|-------------------|------------------------|
| FGFR1 | H93-Y-N95-T       | N102-Y-N104-T     | T90-D-T92-F-G-S95  |
|       | K12-L-L-Y15       | Q56-A-E58-E-R60 | K50-Q-L-R53          |
|       | Y8-K9-A-P-K12 | F17-A-D-P-K21     | N137-Y-T139-A-L        |
|       |                   | K21-R-L-Y24       |                        |
| FGFR3 | P-N22-Y23-K24-P | Y24-C-K26-N     | K50-Q51-L-R53      |
|       | H108-Y-N110-T     | A-N102-Y103-N104-T |                   |
|       | Y30-C-S-N33-G34   |                   |                        |

In bold, peptides identified with 3 interactions with the receptor. The number corresponds to the sequence number of the residue as seen in the PDB file (accession numbers referenced in paragraphs [0023]400291.

By examining the receptor residues that interact with FGF, peptides could be designed ab initio that can complement these amino acids. Due to flexibility, only 4-residues peptides were analyzed. The following peptides were identified; with possible permutations of amino acids at a particular position shown in parenthesis:

FGFR1:
(DE)(KR)(DN)(DEKR)         (SEQ ID NO: 13)

FGFR3:
(DE)(KR)(DNST)(DE)         (SEQ ID NO: 14)

Using the combination virtual screening model based on ligand and protein structural data described above, agonists of FGFR1 and several crystal structures of FGF/FGFR complexes were modeled. This data allowed the design of peptides and docking studies used to prioritize and screen candidate molecules. This screening and testing led to the identification of 13 test peptides that were predicted to exert similar agonist effects as FGF18.

when they are cultured as 3D spheroids. The spatial distribution of the cells is important in order to produce a verisimilar model and the use of spheroidal co-culture of dermal papilla fibroblast (DPF) and keratynocytes (ORSK) is the optimal method to create a µHF.

A scaffold free 3D model of µHF was utilized for these studies, which utilized hanging drop technology and using DPF and ORSK (Italian patent application N° P05838 IT) which presents anagen-like features and can also be pushed through involutive state (catagen-like) representing a valid screening tool for the study phase transition.

To assess the biological activity of the identified set of 13 peptides and their capability to maintain quiescence state, the Vitroscreen µHF standard model has been adapted pushing it in a regressive state (catagen-like) by the application of TGFβ1 to reduce the expression of genes linked to active growth phase (anagen) and to make the model more responsive to FGF18 as quiescence signal.

In particular, in this regressive model, the application of TGFβ1 to 72H induces a catagen-like status with the down-regulation of FGF7 anagen gene and CCND1 as proliferation marker. The subsequent application of FGF18 induces a further decrease of FGF7, CCCND1 and a down-regulation of WNT5b as regulator of anagen epithelial growth. Following this model, the peptides able to mimic the action of FGF18 on gene expression are considered potential retarders of hair follicle regrowth, since they would favor the permanence of the follicle in a resting (telogen state).

The read-out parameters are presented in Table 7.

TABLE 6

13 Selected test peptides for in vitro evaluations according to their potential interaction with FGFR1 and/or FGFR3

| FGFR1 | FGFR3 | FGFR1&FGFR3 |
|---|---|---|
| DRDE (SEQ ID NO: 8) | DKSE (SEQ ID NO: 9) | IEKV (SEQ ID NO: 12) |
| DRLK (SEQ ID NO: 3) | DRTD (SEQ ID NO: 11) | RTGQYK (SEQ ID NO:2) |
| EKDD (SEQ ID NO: 5) | DRV (PEPTIDE NO: 15) | |
| EKTD (SEQ ID NO: 4) | EKND (SEQ ID NO: 7) | |
| KRTG (SEQ ID NO: 6) | KQLR (SEQ ID NO: 1) | |
| | DRVE (SEQ ID NO: 10) | |

Example 2: Co-Culture Hf Test Model

The molecular mechanisms underlying the HF cycle are complex and not fully understood but it is clear that the interactions between the different cellular populations are due to a plethora of regulators and molecules which orchestrate the transition from a phase to the subsequent following a specific scheme.

Studies to evaluate the regulation of the cycle in an in vitro system as a model for screening active compounds able to promote or block the phase transition and, as a consequence, to regulate the hair follicle growth were conducted.

The availability of a DPF-ORSK co-culture model allows investigation of the mechanisms that regulate the HF cycle and to study the effects of active compounds in pre-clinical research. As previously reported, dermal papilla cells deeply modify their gene expression profile when cultured as monolayer, but the transcriptional pattern can be partially restored

TABLE 7

Gene expression analysis by RTqPCR

| Anagen Marker | Function | Effect of FGF18 |
|---|---|---|
| FGF7 | Fibroblast Growth Factor 7; highly expressed during anagen phases, driving hair elongation. Its expression decrease in regressive catagen phase | Decrease (telogen-like) |
| CCND1 | Ciclin 1. Proliferation gene expressed during anagen growth | Decrease (telogen-like) |

TABLE 7-continued

Gene expression analysis by RTqPCR

| Anagen Marker | Function | Effect of FGF18 |
|---|---|---|
| WNT5B | WNT/beta catenin pathway is strictly related to anagen rising. Its expression is increased during telogen to anagen transition | Decrease (telogen-like) |

Efficacy Screening Test-Gene Expression Analysis of Proliferation Anagen Markers
Prediction Model In order to test in vitro the efficacy of synthetic compounds to block anagen rising after telogen quiescence, (since a direct block of hair follicle re-start is not possible in artificial systems), a µHF model system in a regressive state has been developed by the application of TGFβ1 10 ng/ml anticipating that the subsequent application of FGF18 can further suppress anagen markers, mimicking a quiescent (telogen-like phase).

In this scenario, after the sequential application of TGFβ1/FGF18, the expected expression of the anagen marker genes represents the following prediction model:

TABLE 8

Expected Expression of Anagen Marker Genes for Predictive Model

| Anagen Marker | Function | Effect of TGFB1 versus CN | Effect of FGF 18 versus TGFb1 |
|---|---|---|---|
| FGF7 | Fibroblast Growth Factor 7: highly expressed during anagen phases, driving hair elongation. Its expression decreases in regressive catagen phase | Decrease (catagen-like) | Decrease (telogen-like) |
| CCND1 | Ciclin 1. Proliferation gene expressed during anagen growth | Decrease compared (catagen-like) | Decrease (telogen-like) |
| WNT5B | WNT/beta catenin pathway is strictly related to anagen rising. Its expression is increased during telogen to anagen transition | No univocal data are available | Decrease (telogen-like) |

In FIG. 1, the expression of selected genes is reported for a pool of 20 µHF as RQ (relative quantification) value and Error (max and min). FIG. 1 is a graph showing gene expression analysis for the prediction model of regressive µHF for the evaluation of telogen state. RQ values, Error max and min are reported for a pool of 20 µHF. Not treated control CN is used as reference for the relative quantification. The results are summarized as follows:

TGFβ1 10 ng/ml: the application for 72H of the catagen-inducer has reduced, as expected, the expression of FGF7 and CCND1 indicating an efficacy in producing a catagen-like status.

FGF18: the subsequent application of telogen marker FGF18 has shown a dose-dependent effect in enhancing the down regulation of anagen markers. In particular, the concentration of 100 ng/ml induced a further down-regulation of FGF7 and CCND1 as well as a decrease of WNT5b indicating an efficacy in stopping anagen signals and setting the model in a resting, telogen-like status.

Figure 2:
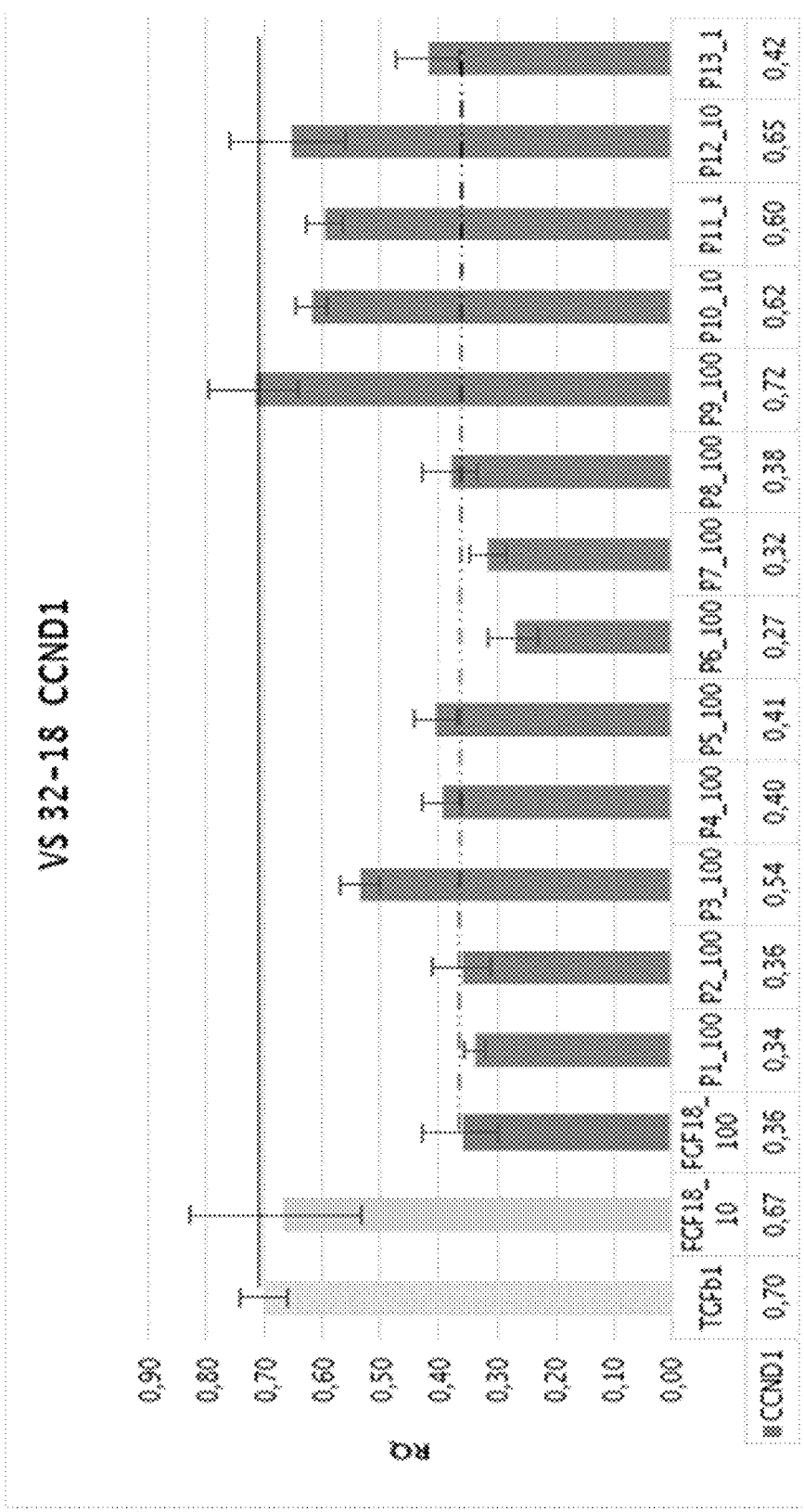
FIG. 2 is a graph showing the CCND gene expression reported for a pool of 20 µHF as RQ (relative quantification) value and Error (max and min) after 24 hours of treatment with peptides at the selected concentration or FGF18 as positive control.

The regressive/telogen-like model by TGFβ1 10 ng/ml/FGF18 100 ng/ml has been validated.
Efficacy Screening Results In FIGS. 2-4, the expression of selected genes is reported for a pool of 20 µHF as RQ (relative quantification) value and Error (max and min) after 24H of treatment with peptides at the selected concentration or FGF18 as positive control. FIG. 2 is a graph showing CCND1 gene expression after 24 h of treatment with peptides or FGF18 in regressive µHF. RQ values, Error max and min are reported. Not treated control CN is used as reference for the relative quantification (not showed). Comparison with TGFβ1 (inducer) is represented by a solid line, comparison with FGF18 100 ng/ml is represented by a dotted line.

TABLE 9

Most relevant effects of the test peptides in comparison with FGF18 100 ng/ml on CCDN1

| Peptide CODE | PEPTIDE | Effect on CCDN1 gene versus FGF18 100 ng/ml | Potential Telogen state maintenance/ growth retard |
|---|---|---|---|
| P6 | SEQ ID NO: 6 | Down-reg. | ++ |
| P1 | SEQ ID NO: 1 | Similar | + |
| P2 | SEQ ID NO: 2 | | + |
| P4 | SEQ ID NO: 4 | | + |
| P5 | SEQ ID NO: 5 | | + |
| P7 | SEQ ID NO: 7 | | + |
| P8 | SEQ ID NO: 8 | | + |
| P13 | PEPTIDE NO: 15 | | + |

The SEQ ID NO:'s, PEPTIDE NO: and P numbers are identical to those listed in Table 1. The P numbers are used in the graphs and data to refer to the test peptides.

Among the tested compounds, compared with FGF18 100 ng/ml, P6 has demonstrated a higher effect in down-regulating proliferation of the CCND1 gene.

Test peptides, P1, P4, P5, P7, P8 and P13 have shown an efficacy comparable to FGF18 100 ng/ml.

Figure 3:
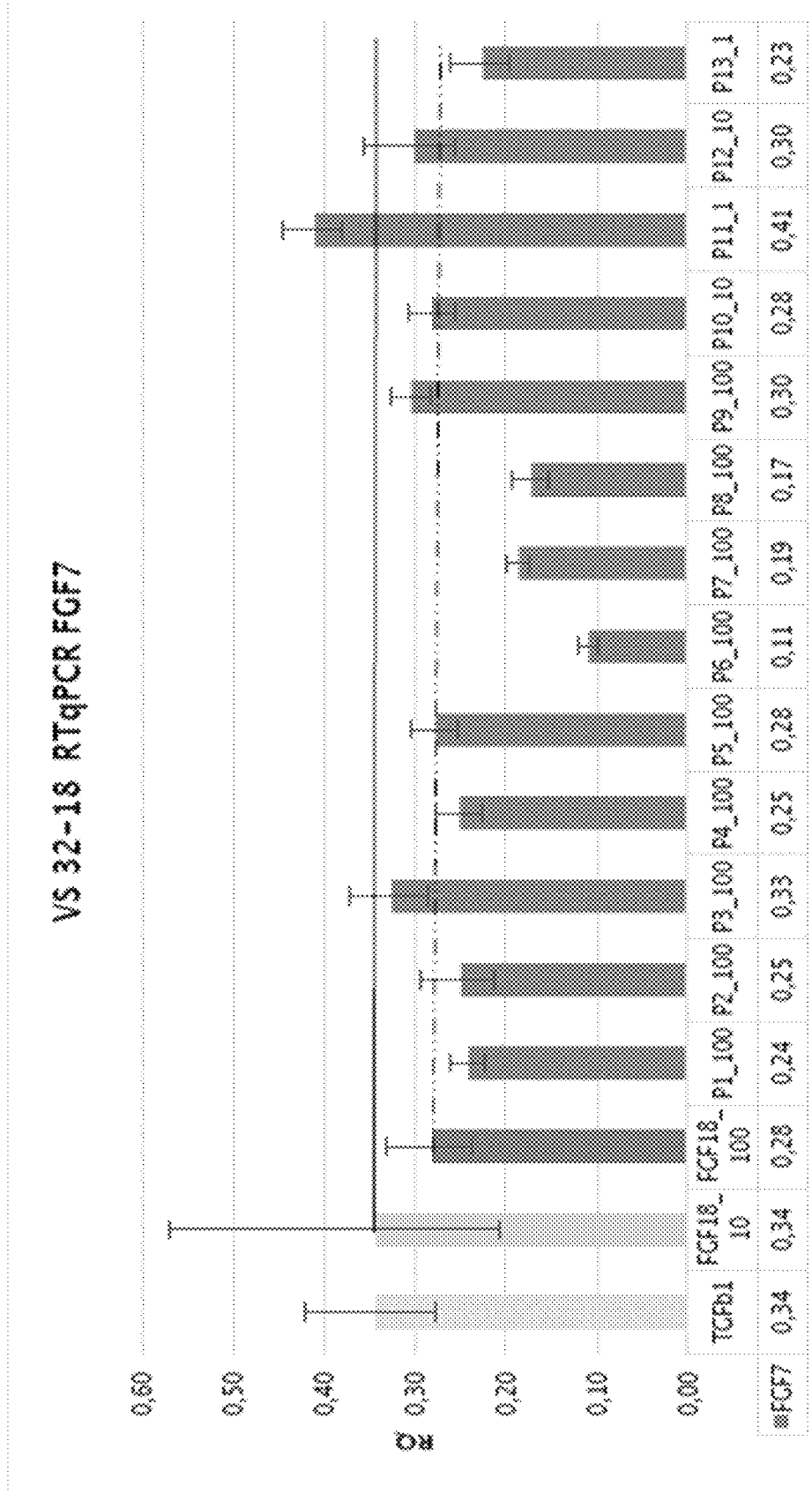
FIG. 3 is a graph showing FGF7 gene expression after 24 hours of treatment with peptides or FGF18 in regressive µHF. RQ values, Error max and min are reported. Not treated control CN is used as reference for the relative quantification (not shown). Comparison with TGFβ1 (inducer) is represented by a solid line, comparison with FGF18 100 ng/ml is represented by a dotted line.

FIG. 3 is a graph showing FGF7 gene expression after 24 h of treatment with the test peptides or FGF18 in regressive µHF. RQ values, Error max and min are reported. Not treated control CN is used as reference for the relative quantification (not showed). Comparison with TGFβ1 (inducer) is represented by line, comparison with FGF18 100 ng/ml is represented by dotted line.

TABLE 10

Summary of the most relevant effects of the test peptides in comparison with FGF18 100 ng/ml on FGF7.

| CODE | PEPTIDE | Effect on FGF7 gene versus FGF18 100 ng/ml | Potential Telogen state maintenance/ growth retard |
|---|---|---|---|
| P6 | SEQ ID NO: 6 | Down-regulation | ++ |
| P7 | SEQ ID NO: 7 | Down-regulation | ++ |
| P8 | SEQ ID NO: 8 | Down-regulation | ++ |
| P1 | SEQ ID NO: 1 | Similar | + |
| P2 | SEQ ID NO: 2 | Similar | + |
| P3 | SEQ ID NO: 3 | Similar | + |
| P4 | SEQ ID NO: 4 | Similar | + |
| P5 | SEQ ID NO: 5 | Similar | + |
| P9 | SEQ ID NO: 9 | Similar | + |
| P10 | SEQ ID NO: 10 | Similar | + |
| P13 | PEPTIDE NO: 15 | Similar | + |

Among the tested compounds, compared with FGF18 100 ng/ml peptides P6, P7 and P8 have shown higher effect in switch off FGF7 gene (anagen). Peptides P1-P5, P9, P11 and P13 have exerted an action similar to FGF18 100 ng/ml.

Figure 4:
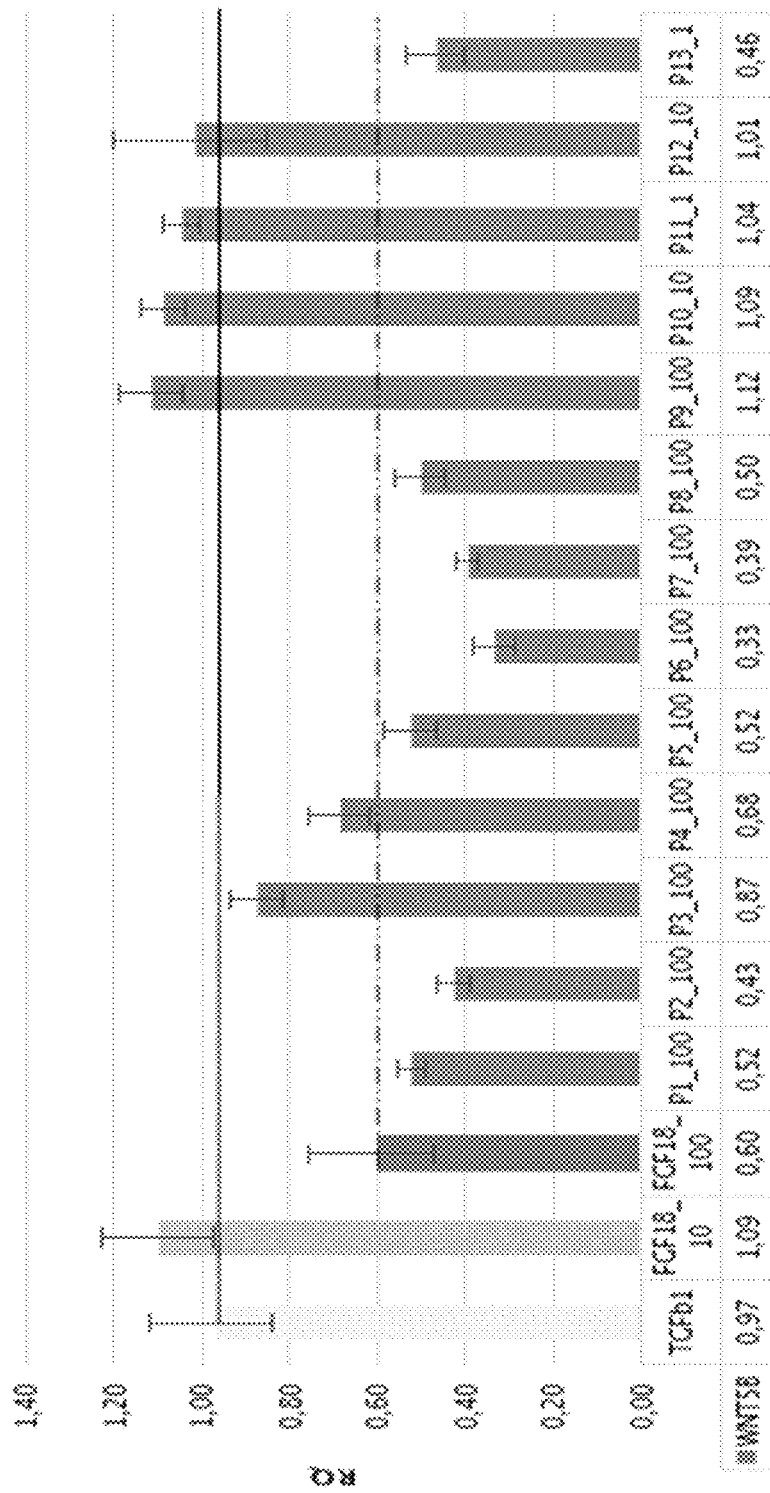
FIG. 4 is a graph showing the expression level of WNT5B reported for a pool of 20 µHF as RQ (relative quantification) value and Error (max and min) after 24 hours of treatment with peptides at the selected concentration or FGF18 as positive control. Comparison with TBGβ1 (inducer) is shown with a solid line, and comparison with FGF18 100 ng/ml is shown with a dotted line.

FIG. 4 is a graph showing WNT5B gene expression after 24 h of treatment with test peptides or FGF18 in regressive μHF. RQ values, Error max and min are reported. Not treated control CN is used as reference for the relative quantification (not showed). Comparison with TGFβ1 (inducer) is represented by line, comparison with FGF18 100 ng/ml is represented by dotted line. The most relevant effects of the test peptides in comparison with FGF18 100 ng/ml on WNT5B are:

TABLE 11

Effects of test peptides on WNT5B

| CODE | PEPTIDE | Effect on WNT5B gene versus FGF18 100 ng/ml | Potential Telogen state maintenance/ growth retard |
|---|---|---|---|
| P2 | SEQ ID NO: 2 | Down-regulation | ++ |
| P6 | SEQ ID NO: 6 | Down-regulation | ++ |
| P7 | SEQ ID NO: 7 | Down-regulation | ++ |
| P1 | SEQ ID NO: 1 | Similar | + |
| P4 | SEQ ID NO: 4 | Similar | + |
| P5 | SEQ ID NO: 5 | Similar | + |
| P8 | SEQ ID NO: 8 | Similar | + |
| P13 | PEPTIDE NO: 15 | Similar | + |

Among the tested compounds, compared with FGF18 100 ng/ml, P2, P6 and P7 have shown higher effect in down-regulating WNT5b indicating an inhibitory effect on the growth of epithelial compartment linked to telogen resting phase.

Test peptides P1, P4, P5, P8 and P13 have exerted an action similar to FGF18 100 ng/ml.

The μHF model has been used for a screening study with the aim to characterize the 13 peptides designed on the basis of FGF18 structure in order to mimic its biological function in retarding hair growth. The following test items have been evaluated after the selection of test concentration in a preliminary tox assay.

TABLE 12

Preliminary Tox Assay Peptide Concentrations

| NAME | Peptide CODE | TESTED CONCENTRATION (ng/mL) |
|---|---|---|
| SEQ ID NO: 1 | P1 | 100 |
| SEQ ID NO: 2 | P2 | 100 |
| SEQ ID NO: 3 | P3 | 100 |
| SEQ ID NO: 4 | P4 | 100 |
| SEQ ID NO: 5 | P5 | 100 |
| SEQ ID NO: 6 | P6 | 100 |
| SEQ ID NO: 7 | P7 | 100 |
| SEQ ID NO: 8 | P8 | 100 |
| SEQ ID NO: 9 | P9 | 100 |
| SEQ ID NO: 10 | P10 | 10 |
| SEQ ID NO: 11 | P11 | 1 |
| SEQ ID NO: 12 | P12 | 10 |
| PEPTIDE NO: 15 | P13 | 1 |

The gene expression analysis of proliferation/anagen markers and the possible effects of the test peptides in maintaining telogen phase and, as a consequence, retarding anagen rising and hair growth can be summarized in Table 13.

TABLE 13

Effect of the test peptides on the expression of proliferation/anagen markers in order to mimic a FGF18 effect and promoting telogen phase/retarding anagen.

| | | | Potential effect on telogen phase induction/growth retard | | |
|---|---|---|---|---|---|
| Peptide | | | | | |
| CODE | PEPTIDE | ng/ml | CCDN1 | FGF7 | WNT5b |
| P1 | SEQ ID NO: 1 | 100 | + | + | + |
| P2 | SEQ ID NO: 2 | 100 | + | + | ++ |
| P3 | SEQ ID NO: 3 | 100 | no | + | no |
| P4 | SEQ ID NO: 4 | 100 | + | + | + |
| P5 | SEQ ID NO: 5 | 100 | + | + | + |
| P6 | SEQ ID NO: 6 | 100 | ++ | ++ | ++ |
| P7 | SEQ ID NO: 7 | 100 | + | ++ | ++ |
| P8 | SEQ ID NO: 8 | 100 | + | ++ | + |
| P9 | SEQ ID NO: 9 | 100 | no | + | no |
| P10 | SEQ ID NO: 10 | 10 | no | + | no |
| P11 | SEQ ID NO: 11 | 1 | no | no | no |
| P12 | SEQ ID NO: 12 | 10 | no | no | no |
| P13 | PEPTIDE NO: 15 | 1 | + | + | + |

(++) higher effect in comparison with FGF18 100 ng/ml.
(+) effect comparable to FGF18 100 ng/ml.

The different peptides have shown different efficacy in their ability to mimic FGF18's activity, most likely due to differences in molecular structure, and can be grouped on the basis of a decreasing efficacy as follows:

1. Highest efficacy: Peptide P6 (SEQ ID NO:6) and P7 (SEQ ID NO:7) have shown the highest efficacy compared with reference FGF18 100 ng/ml for at least 2 of 3 of the considered genes.
2. High efficacy: P2 (SEQ ID NO:2) and P8 (SEQ ID NO:8) have shown higher efficacy for one marker in comparison with FGF18 100 ng/ml.
3. FGF18-like efficacy: P1 (SEQ ID NO:1), P4 (SEQ ID NO:4), P5 (SEQ ID NO:5), P13 (PEPTIDE NO:15) have shown an efficacy comparable with FGF18 100 ng/ml.
4. No efficacy: P3 (SEQ ID NO:3), P9 (SEQ ID NO:9), P10 (SEQ ID NO:10), P11 (SEQ ID NO:11) P12 (SEQ ID NO:12) have not shown any relevant efficacy in mimic FGF18 100 ng/ml.

Methods and Materials

Cytotoxicity Testing

Cytotoxicity testing has been performed on μHF at day 3 in order to select the testing concentration of peptides for the following screening assays.

Treatments: Negative control: 1 (not treated), Positive control: FGF18 100 ng/ml, Treatments: 39 (13 peptides, 3 concentrations each: 1-10-100 ng/ml), Biological replicates: 5 μHF for each treatment, Time-point: 1 (after 24 H of treatment), Read-out parameters: Viability by ATP Cytotoxicity Protocol The test items have been tested at 3 concentrations/each for their cytotoxicity potential after 24 h exposure on μHF. FGF18 100 ng/ml have been used as positive control. The toxicity has been evaluated by ATP release on n=5 μHF.

TABLE 14

| Cytotoxicity Protocol | | | | | | | |
|---|---|---|---|---|---|---|---|
| | Days | | | | | | |
| MTs Culture | 1<br>P0 | 2<br>P1 | 3<br>P2 | 4<br>P3 T1 | 5<br>T2 | 6<br>T3 | 7<br>T4 |
| HHDPC cell seeding | X | | | | | | |
| HEPK cell seeding | | | | X | | | |
| Transfer in GravityTrap | | | | | | X | |
| Test item Application (24 H) | | | | | | X | |
| ATP | | | | | | | X |

P = DAYS IN GRAVITY PLUS
T = DAYS IN GRAVITY TRAP

Efficacy Screening Test

After the selection of test concentrations of the peptides, efficacy was performed on regressing µHF (TGFβ1 treated) at day 5 in order to evaluate the further efficacy of peptides to decrease the gene expression of proliferation (CCND1) and anagen marker (FGF7). The potential down-regulation of epithelial growth regulator WNT5B has been evaluated as an optional parameter.

Treatments: Negative control: 1 (not treated), Regression inducer: TGFβ1 10 ng/ml, Positive control: FGF18 10-100 ng/ml, Treatments: 13 peptides (1 concentration each), Biological replicates: 1 biological replicates from pool of 20 µHF, Time-point: after 72H of TGFβ1 induction followed by 24H of peptide or FGF18 application, Read-out parameters: 1 Proliferation gene (CCND1) by RTqPCR, 2 anagen regulators (FGF7, WNT5B) by RTqPCR Protocol in brief: The µHFs were harvested in Gravity Trap plates and treated for 72 h with TGFβ1 10 ng/ml to induce regression phase. After this period, the µHFs were treated with negative control, FGF 18 10-100 ng/ml or test items at the selected concentration in the medium. After exposure, a pool of 20 µHF for each treatment has been harvested for gene expression analysis.

Expected results: The application of TGFβ1 down-regulates the expression of the anagen key-factors confirming the involution of the model. The reference—FGF18 enhances the down-regulation of the genes of proliferation and anagen promoters in comparison with in comparison with TGFβ1. The efficacy of each compound in inhibiting proliferation and anagen markers has been assessed in comparison with FGF18.

TABLE 15

| Efficacy of Peptide Compounds in Inhibiting Proliferation and Anagen Maskers | | | | | | | | | | | | |
|---|---|---|---|---|---|---|---|---|---|---|---|---|
| | Days | | | | | | | | | | | |
| MTs Culture | 1<br>P0 | 2<br>P1 | 3<br>P2 | 4<br>P3 | 5<br>P4 | 6<br>P5 | 7<br>P6 T1 | 8<br>T2 | 9<br>T3 | 10<br>T4 | 11<br>T5 | 12<br>T6 |
| HHDPC cell seeding | X | | | | | | | | | | | |
| HEPK cell seeding | | | X | | | | | | | | | |
| Trasfer in GravityTrap | | | | | | | X | | | | | |
| Change medium/Treatment Application TGFβ1 10 ng/ml (72 H) | | | | | | | | X | | | | |
| Change medium/Treatment Application Test Items or FGF18 24 H | | | | | | | | | | X | | |
| Collection for RTqPCR | | | | | | | | | | | | X |

P = DAYS IN GRAVITY PLUS,
T = DAYS IN GRAVITY TRAP

Test System—Human Reconstituted µHF

The µHF microtissue were reconstructed using the hanging drop method into GRAVITY$^{PLUS}$ plates from InSphero (Switzerland) using fibroblasts and keratinocytes from human origin. The MTs were Transferred in GRAVITYTRAP for treatments and manipulation. Culture conditions: incubator at 37° C., 5% CO2, saturated humidity with adequate culture medium. The Fibroblast batch and keratinocytes has been tested for the absence of HIV, Hepatitis B, Hepatitis C, Mycoplasma. The maintenance medium has been tested for sterility.

TABLE 16

| | Cell Sources |
|---|---|
| | TA |
| NAME and BATCH/ SUPPLIER | Adult HHDPC (Dermal Papilla Fibroblast) cat. P10881 batch. 9583 |
| MANUFACTURER | Innoprot |
| DONOR DATA: | SEX: FEMALE |
| | TISSUE SOURCE: SCALP |
| | AGE: 53 YEARS |
| | RACE: ADULT WHITE |
| NAME and BATCH/ SUPPLIER | Adult HPEKp (Human Keratinocytes) cat. HPEKp batch. MC1708172 |
| MANUFACTURER | Cellntech |
| DONOR DATA: | SEX: n.a. |
| | TISSUE SOURCE: Epithelia, 3 donor pool |
| | AGE: juvenile |
| | RACE: n.a. |

Test Items: Identification and Characterization

The tested concentrations have been selected on the basis of preliminary tox test, stating a range of 1-10-100 ng/ml on medium.

TABLE 17

Tested Peptide Concentrations and Storage Conditions

| PRODUCER | BATCH | PEPTIDE | STORAGE | TESTED CONCENTRATION ng/mL | SOLVENT |
|---|---|---|---|---|---|
| GreenPharma | ND | SEQ ID NO: 1 | −20° C. | 100 | Culture Medium |
| GreenPharma | ND | SEQ ID NO: 2 | −20° C. | 100 | Culture Medium |
| GreenPharma | ND | SEQ ID NO: 3 | −20° C. | 100 | Culture Medium |
| GreenPharma | ND | SEQ ID NO: 4 | −20° C. | 100 | Culture Medium |
| GreenPharma | ND | SEQ ID NO: 5 | −20° C. | 100 | Culture Medium |
| GreenPharma | ND | SEQ ID NO: 6 | −20° C. | 100 | Culture Medium |
| GreenPharma | ND | SEQ ID NO: 7 | −20° C. | 100 | Culture Medium |
| GreenPharma | ND | SEQ ID NO: 8 | −20° C. | 100 | Culture Medium |
| GreenPharma | ND | SEQ ID NO: 9 | −20° C. | 100 | Culture Medium |
| GreenPharma | ND | SEQ ID NO: 10 | −20° C. | 10 | Culture Medium |
| GreenPharma | ND | SEQ ID NO: 11 | −20° C. | 1 | Culture Medium |
| GreenPharma | ND | SEQ ID NO: 12 | −20° C. | 10 | Culture Medium |
| GreenPharma | ND | PEPTIDE NO: 15 | −20° C. | 1 | Culture Medium |

TABLE 18

Negative and Positive Controls

| | REGRESSION INDUCER | POSITIVE CONTROL 1 | POSITIVE CONTROL 2 |
|---|---|---|---|
| NAME | Transforming Growth Factor Beta 1 | Fibroblast Growth Factor 18 | Fibroblast Growth Factor 18 |
| UNIVOCAL CODE | TGFβ1 | FGF18_10 | FGF18_100 |
| MANUFACTURER REF. | Sigma Aldrich T7039 | Sigma Aldrich T7301 | Sigma Aldrich T7301 |
| BATCH | SLBT3107 | SLBP5329V | SLBP5329V |
| CONCENTRATION OF USE | 10 ng/ml | 10 ng/ml | 100 ng/ml |
| STORAGE | −20° C. | −20° C. | −20° C. |

Methods—Viability Assay By ATP Measurement

The kit CellTiter Glo® (Promega) Luminescent cell Viability Assay is used for Adenosine-5- triphosphate (ATP) quantification. The assay procedures involves adding the single reagent directly to MTs cultured in medium. The cell lysis and the generation of a luminescent signal is proportional to the amount of ATP present. ATP measurements have been performed on 5 biological replicates and mean and standard deviation have been calculated. The threshold of 50% viability in comparison to negative control have been used as cut off; the max concentration possible over threshold has been used for the efficacy screening test.

Nucleic Acid Extractions And Gene Expression Analysis

RNA Extraction

The MTs have been lysed in proper buffer and the extraction of the nucleic acids was performed using RNAqueous kit (Ambion, Life Technologies) following the manufactures' instructions. RNA was eluted in RNAse free water, quantified by spectrophotometric assay and stored at −80° C. until use.

Retrotranscription and PCR

The High Capacity cDNA Reverse Transcription kit was used to synthetize cDNA from extracted RNA. The instrument Applied Biosystems 7500 Fast Real Time PCR with fluorescent-based PCR chemistry, the TaqMan assay, was used to study gene expression of significant biomarkers. The change in the expression of specific genes in treated samples can be measured as Relative Quantification in comparison with a calibrator (not treated) sample. For each sample, a pool of 20 Mts has been used for the analysis using the following TaqMAN assays:

TABLE 19

TAqMAN assays

| CCND1 | Hs00277039_m1 | 1493446 |
|---|---|---|
| FGF7 | Hs00384281_m1 | 1245545 |
| GAPDH | Hs99999905_m1 | 1583192 |
| WNT5B | Hs01086864_m1 | 1556647 |

Data Acquisition and Acceptance Criteria

Fluorescence data of the RT-PCR generated by the thermocycler ABI 7500 Fast, are collected by the internal software SDS 2.0.6 and the Raw Data (RQ study results) are printed and exported in Excel.

These data contained the following information: Biological group, Target, Omitted, Technical replicates, RQ, RQ Min, RQ Max. Because each cycle in the PCR reaction corresponds to a 2-fold increase in PCR product, a difference of one in threshold cycle number represents at least 2-fold difference in the expression of a particular gene compared to the calibrator sample and can be considered as significant. The 95% of confidence level is used by the software to calculate the errors.

A value has been accepted as significant when the gene is "one fold" up (RQ>2) or down regulated (RQ<0,5) compared to the calibrator sample (RQ=1). The internal instrument level of confidence used is 95%.

Cytotoxicity Testing

ATP Content During the Proto-Hair Culture

Table 20 shows the mean ATP content (nM) in μHF after 24H of treatment with FGF18 100 ng/ml or different concentrations of peptides (1-10-100 ng/ml). For each peptide, the selected concentration for efficacy screening test has been indicated.

TABLE 20

Mean ATP content (nM) in μHF after 24 H treatment.

| | ATP nM |
|---|---|
| CN | 1306.1 |
| FGF18 100 | 1560.3 |
| P1_1 | 1876.5 |
| P1_10 | 2007.2 |
| P1_100 | 1903.1 |
| P2_1 | 1522.4 |
| P2 10 | 1838.6 |
| P2 100 | 1687.8 |
| P3_1 | 1026.2 |

TABLE 20-continued

Mean ATP content (nM) in μHF after 24 H treatment.

| | ATP nM |
|---|---|
| P3 10 | 924.8 |
| P3 100 | 1631.2 |
| P4 1 | 1567.7 |
| P4 10 | 1715.2 |
| P4 100 | 1597.4 |
| P5 1 | 1263.3 |
| P5 10 | 1108.9 |
| P5 100 | 1255.5 |
| P6 1 | 1122.0 |
| P6 10 | 1116.0 |
| P6 100 | 1313.3 |
| P7 1 | 1275.4 |
| P7 10 | 1243.9 |
| P7 100 | 1258.8 |
| P8_1 | 1148.5 |
| P8 10 | 1155.5 |
| P8 100 | 1229.3 |
| P9_1 | 1521.4 |
| P9 10 | 1273.6 |
| P9 100 | 1469.4 |
| P10 1 | 1727.8 |
| P10 10 | 1706.1 |
| P10 100 | 1329.1 |
| P11_1 | 463.1 |
| P11_10 | 447.0 |
| P11_100 | 149.0 |
| P12 1 | 435.7 |
| P12 10 | 562.8 |
| P12 100 | 370.0 |
| P13 1 | 576.0 |
| P13 10 | 516.6 |
| P13 100 | 404.1 |

N = 5 μHF. Selected concentrations for screening test are reported in bold.

For the selection of test concentrations of each peptide, the 50% ATP content in comparison with negative (not treated) control has been selected as threshold. The higher concentration over the selected threshold has been used for efficacy screening test for peptides form P1 to P9.

In case of P10 the highest ATP content has been measured at 10 ng/ml even if all the values were over the threshold.

Peptides P11, P12, and P13 have shown an under-threshold content of ATP indicating a potential adverse effect in μHF viability. In order to assess the efficacy of these peptides in comparison with FGF18 and the other test elements, the highest possible concentration in the proposed range (1-10-100 ng/ml) was selected.

General Methods

Standard methods in molecular biology are described Sambrook, Fritsch and Maniatis (1982 & 1989 2nd Edition, 2001 3rd Edition) Molecular Cloning, A Laboratory Manual, Cold Spring Harbor Laboratory Press, Cold Spring Harbor, N.Y.; Sambrook and Russell (2001) Molecular Cloning, 3rd ed., Cold Spring Harbor Laboratory Press, Cold Spring Harbor, N.Y.; Wu (1993) Recombinant DNA, Vol. 217, Academic Press, San Diego, Calif.). Standard methods also appear in Ausbel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, NY, pp. 16.0.5-16.22.17; Sigma-Aldrich, Co. (2001) Products for Life Science Research, St. Louis, Mo.; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) Current Protcols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) Current Protocols in Immunology, Vol. 4, John Wiley, Inc., New York).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

Example 3: Investigation of FGF18 Expression in Human Hair Follicles and Whether FGF18 or FGF18-Like Peptides Stimulate Catagen and Maintain Hair Follicles in Telogen FGF18 is expressed by bulge of anagen and telogen HFs in mice, and treatment of bulge KCs inhibit their growth (Blanpain et al., Cell 2004). In addition, FGF18 mRNA is expressed by the dermal papilla of mouse telogen HFs, especially during early telogen (Greco et al., Cell Stem Cell 2009). Additional experiments confirmed that FGF18 is important to maintain telogen HFs in the quiescent phase (Kimura-Ueki et al., J Invest Dermatol 2012, Plikus et al., J Invest Dermatol 2012) and that this is a target gene of Foxp1 in mice (Leishman et al., Dev 2013). The receptor of FGF18 in mice, i.e. FGFR3c and FGFR4, are also expressed by the hair follicle epithelium (Kimura-Ueki et al., J Invest Dermatol 2012). However, whether FGF18 regulates human hair follicle biology remains basically unknown. It has been shown that in anagen hair follicles, FGF18 mRNA is mainly expressed in the suprabulbar outer root sheath and less in the bulge (Ohyama et al., J Clin Invest 200), and that its receptor, i.e. FGF3R is expressed by human anagen HFs (Takenaka et al., Arch Derm Res 2002). In vitro cell culture showed that only human dermal papilla and not outer root sheath keratinocytes responded to FGF18 (Kawano et al., J Invest Dermatol 2005). However, the effect of FGF18 on anagen, catagen, and telogen human HFs remains to be investigated.

Therefore, the overall aim of the current project is to investigate whether FGF18 maintains telogen quiescence also in human hair follicles, and possibly also stimulates catagen development with the ultimate goal to use FGF18-like peptides as cosmetic agents to inhibit hair regrowth.

Experimental Plan:

Step 1: Investigate whether FGF18 and/or a selected FGF18-like peptide modulates anagen/catagen conversion ex vivo in human HFs. Since most of the hair follicles in our body are in the growth phase (anagen), a good product for inhibiting hair growth should promote catagen or at least not prolong anagen. Therefore, this investigation will confirm whether FGF18 or a selected FGF18-like peptide does not prolong anagen and possibly promotes catagen. In addition, we will investigate whether the FGF18-like peptide blocks hair follicles in a specific catagen phase as indication of retardation of new anagen initiation.

Human microdissected anagen and early catagen full-length hair follicle organ culture ex vivo will be performed and evaluation of HF elongation, anagen/catagen conversion, different catagen phases, and activity of bulge stem cells (Alam et al., Br J Dermatol 2019). One experiment (One donor): 25-30 microdissected anagen HFs and remaining early catagen HFs from the same donor, 4 experimental groups (vehicle, one selected concentration of FGF18, two selected concentrations of the FGF18-like peptide).

Parameters to be evaluated during the culture: Hair follicle elongation (hair shaft production) ex vivo (digital brightfield microscope) in anagen HFs only.

Parameters to be evaluated in situ (day6): Hair cycle staging and scoring (Ki-67/TUNEL immunofluorescence, and Masson Fontana histochemistry), Hair matrix keratinocyte proliferation and apoptosis (Ki-67/TUNEL immunofluorescence), Melanin clumping in the hair follicle pigmentary unit (Masson Fontana histochemistry), Number and proliferation of K15+ cells in the bulge (K15/Ki-67 immunofluorescence).

Step 2: Investigate whether FGF18 is important to maintain telogen quiescence in human HFs. This investigation will provide results whether FGF18 neutralization induces activation of signalling pathways involved in telogen/anagen conversion in human telogen HFs.

Human microdissected telogen full-length hair follicle organ culture ex vivo will be performed and evaluation of activity of bulge stem cells, and activation of Wnt signalling (Hernandez et al., J Am Acad Dermatol 2018; Hawkshaw et al., Br J Dermatol 2019). One experiment (One donor): 2-6 microdissected telogen HFs, 2 experimental groups (vehicle, one selected concentration of FGF18 neutralizing antibody or FGF3R antagonist), EdU 4 hours pre-treatment before starting treatment.

Parameters to be evaluated in situ (day6): Hair cycle staging (Ki-67/TUNEL immunofluorescence), Number and proliferation of K15+ cells in the bulge (K15/Ki-67 immunofluorescence), Expression of Lef-1 in the secondary hair germ (Lef-1 in situ hybridization).

Step 3: Characterize the protein expression of FGF18, and FGFR3 in human anagen, catagen, and telogen HFs. This investigation will help provide data whether FGF18, and FGFR3 are expressed in human HFs to confirm that these can be targeted for hair growth management.

Single immunostainings for FGF18, and FGFR3 will be established, and executed in clinically "healthy" anagen, catagen, and telogen HFs from at least n=3 healthy donors either using freshly embedded scalp skin or follicular units (Alam et al., Br J Dermatol 2019).

Step 4: Characterize the mRNA expression in situ of FGF18 in human anagen, catagen, and telogen HFs. This investigation will provide data on which cells are indeed producing FGF18 in human HFs to speculate a possible role of FGF18 on human hair follicle biology.

In situ hybridization for FGF18 will be established, and executed in clinically "healthy" anagen, catagen, and telogen HFs from at least n=3 healthy donors either using freshly embedded scalp skin or follicular units (Hawkshaw et al., Br J Dermatol 2019).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A topical composition comprising an effective amount of a fibroblast growth factor 18 (FGF18) agonist peptide consisting of an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO: 7, SEQ ID NO: 8, SEQ ID NO:9, SEQ ID NO:10, SEQ ID NO:11, SEQ ID NO:12, DRV, and combinations thereof, and a cosmetically acceptable excipient, wherein the topical composition is formulated as a lotion, cream, serum, spray, mousse, aerosol, emulsion, cake, ointment, gel, paste, patch, pencil, towelette, mask, stick, foam, elixir, oil-in-water emulsion (O/W), water-in-oil (W/O) emulsion, microemulsion, or concentrate.

2. The topical composition of claim 1, wherein the effective amount of one of more fibroblast growth factor 18 (FGF18) agonist peptides is about 0.00001% to about 1% w/w in the topical composition.

3. The topical composition of claim 1, wherein the effective amount of one of more fibroblast growth factor 18 (FGF18) agonist peptides is about 1 ng/ml to about 100 ng/ml in the topical composition.

4. The topical composition of claim 1, wherein the effective amount of one of more fibroblast growth factor 18 (FGF18) agonist peptides is about 1 uM to about 10 uM in the topical composition.

5. The topical composition of claim 1, wherein the effective amount of one of more fibroblast growth factor 18 (FGF18) agonist peptides is about 0.01 ug to about 1000 ug in the topical composition.

6. The topical composition of claim 1, wherein the cosmetically acceptable excipient is selected from the group consisting of a diluent, a solvent, a surfactant, a thickening agent, a foaming agent, a gelling agent, an emulsifier, a water soluble vehicle, a hydrophobic vehicle, a viscosity modifier, an antioxidant, a buffer, a skin protectant, a chelating agent, a fragrance, a preservative, a surfactant, a lubricant, a penetration enhancer, a humectant, a moisturizer, a solubilizer, a plasticizer, a propellant, an alcohol, an emollient, and combinations thereof.

7. The topical composition of claim 1, wherein the cosmetically acceptable excipient includes glycerin, water, and sodium levulinate.

8. The topical composition of claim 1, wherein the topical composition further comprises an agent selected from the group consisting of a lathering surfactant, a moisturizer, an anti-dandruff agent, a vitamin, a hydroxy acid, a chemical or physical sunscreen, an antioxidant, a retinoid, a progesterone, and combinations thereof.

9. A topical composition comprising:
(i) an effective amount of a fibroblast growth factor 18 (FGF18) agonist peptide consisting of:
    (a) an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO: 7, SEQ ID NO: 8, SEQ ID NO:9, SEQ ID NO:10, SEQ ID NO:11, SEQ ID NO:12, DRV, and combinations thereof; and
    (b) a protection group linked at the N-terminus of the amino acid sequence, wherein the protection group is selected from the group consisting of: an acetyl group, a fluorenyl methoxy carbonyl group, a formyl group, a palmitoyl group, a myristyl group, a stearyl group, a linoleate group, a polyethylene glycol (PEG), and other cosmetically acceptable protecting groups; and
(ii) a cosmetically acceptable excipient, wherein the topical composition is formulated as a lotion, cream, serum, spray, mousse, aerosol, emulsion, cake, ointment, gel, paste, patch, pencil, towelette, mask, stick, foam, elixir, oil-in-water emulsion (O/W), water-in-oil (W/O) emulsion, microemulsion, or concentrate.

10. A method for decreasing, or eliminating hair growth in a subject comprising topically administering to a target location on the subject a topical composition comprising an effective amount of one or more fibroblast growth factor 18 (FGF18) agonist peptides consisting of amino acid sequences selected from the group consisting of SEQ ID NO:1, SEQ ID NO: 2, SEQ ID NO:3, SEQ ID NO:4, SEQ ID NO:5, SEQ ID NO: 6, SEQ ID NO: 7, SEQ ID NO: 8, SEQ ID NO:9, SEQ ID NO:10, SEQ ID NO:11, SEQ ID NO:12, DRV, and combinations thereof, and a cosmetically acceptable excipient, wherein the topical composition is formulated as a lotion, cream, serum, spray, mousse, aerosol, emulsion, cake, ointment, gel, paste, patch, pencil, towelette, mask, stick, foam, elixir, oil-in-water emulsion (O/W), water-in-oil (W/O) emulsion, microemulsion, or concentrate.

11. The method of claim 10, wherein the effective amount of one of more fibroblast growth factor 18 (FGF18) agonist peptides is about 0.00001% to about 1% w/w in the topical composition.

12. The method of claim 10, wherein the effective amount of one of more fibroblast growth factor 18 (FGF18) agonist peptides is about 1 ng/ml to about 100 ng/ml in the topical composition.

13. The method of claim 10, wherein the effective amount of one of more fibroblast growth factor 18 (FGF18) agonist peptides is about 1 uM to about 10 uM in the topical composition.

14. The method of claim 10, wherein the effective amount of one of more fibroblast growth factor 18 (FGF18) agonist peptides is about 0.01 ug to about 1000 ug in the topical composition.

15. The method of claim 10, further comprising administering a second skin care composition to the target location after the topical composition is applied.

16. The method of claim 10, wherein the target location is selected from the group consisting of scalp, face, body, eyebrow, and combinations thereof.

17. The method of claim 10, wherein the target location does not normally grow hair.

18. The method of claim 10, wherein the topical composition further comprises an agent selected from the group consisting of a lathering surfactant, a moisturizer, an anti-dandruff agent, a vitamin, a hydroxy acid, a chemical or physical sunscreen, an antioxidant, a retinoid, and a progesterone.

19. The method of claim 10, wherein the topical composition is administered daily, weekly, twice weekly, every two weeks, every three weeks, or monthly.

20. The method of claim 10, wherein the topical composition is administered using an applicator device.

\* \* \* \* \*

SEQUENCE LISTING

```
<160> NUMBER OF SEQ ID NOS: 14

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Lys Gln Leu Arg
1

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
```

```
<400> SEQUENCE: 2

Arg Thr Gly Gln Tyr Lys
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Asp Arg Leu Lys
1

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Glu Lys Thr Asp
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide

<400> SEQUENCE: 5

Glu Lys Asp Asp
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6

Lys Arg Thr Gly
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide

<400> SEQUENCE: 7

Glu Lys Asn Asp
1

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide
```

```
<400> SEQUENCE: 8

Asp Arg Asp Glu
1

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide

<400> SEQUENCE: 9

Asp Lys Ser Glu
1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

Asp Arg Val Glu
1

<210> SEQ ID NO 11
<211> LENGTH: 4
<212> TYPE: PRT
<213> ORGANISM: Artificial Sequence
<220> FEATURE:
<223> OTHER INFORMATION: Synthetic peptide

<400> SEQUENCE: 11

Asp Arg Thr Asp
1

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide

<400> SEQUENCE: 12

Ile Glu Lys Val
1

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Asp Glu Lys Arg Asp Asn Asp Glu Lys Arg
1               5                   10
```

```
<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Asp Glu Lys Arg Asp Asn Ser Thr Asp Glu
1               5                   10
```